(12) United States Patent
Otillar et al.

(10) Patent No.: US 9,153,300 B2
(45) Date of Patent: Oct. 6, 2015

(54) SYSTEM AND METHODS FOR LOCALIZING AND ANALYZING SAMPLES ON A BIO-SENSOR CHIP

(75) Inventors: Robert Otillar, Los Altos, CA (US);
David Storek, Gothenburg (SE);
Christer Johansson, Gothenburg (SE)

(73) Assignee: Robert P. Otillar, Mountain View, CA (US)

( * ) Notice: Subject to any disclaimer, the term of this patent is extended or adjusted under 35 U.S.C. 154(b) by 468 days.

(21) Appl. No.: 13/136,978

(22) Filed: Aug. 15, 2011

(65) Prior Publication Data

US 2012/0172260 A1 Jul. 5, 2012

Related U.S. Application Data

(63) Continuation of application No. 09/683,861, filed on Feb. 22, 2002, now Pat. No. 7,998,746, which is a continuation-in-part of application No. 09/963,866, filed on Sep. 26, 2001, now abandoned, which is a continuation of application No. 09/938,471, filed on Aug. 23, 2001, now abandoned.

(60) Provisional application No. 60/228,015, filed on Aug. 24, 2000.

(51) Int. Cl.
| | |
|---|---|
| *G01N 35/10* | (2006.01) |
| *G11C 7/10* | (2006.01) |
| *B01J 19/00* | (2006.01) |
| *B01L 3/00* | (2006.01) |
| *G01N 27/74* | (2006.01) |
| *G06F 7/72* | (2006.01) |
| *G01N 35/00* | (2006.01) |
| *C40B 40/06* | (2006.01) |
| *C40B 60/14* | (2006.01) |

(52) U.S. Cl.
CPC ........... *G11C 7/1066* (2013.01); *B01J 19/0046* (2013.01); *B01L 3/502738* (2013.01); *B01L 3/502761* (2013.01); *G01N 27/745* (2013.01); *G06F 7/723* (2013.01); *B01J 2219/005* (2013.01); *B01J 2219/0034* (2013.01); *B01J 2219/00317* (2013.01); *B01J 2219/00439* (2013.01); *B01J 2219/00459* (2013.01); *B01J 2219/00585* (2013.01); *B01J 2219/00596* (2013.01); *B01J 2219/00605* (2013.01); *B01J 2219/00612* (2013.01); *B01J 2219/00648* (2013.01); *B01J 2219/00659* (2013.01); *B01J 2219/00722* (2013.01); *B01L 2300/049* (2013.01); *B01L 2400/0633* (2013.01); *C40B 40/06* (2013.01); *C40B 60/14* (2013.01); *G01N 35/0098* (2013.01); *G01N 2035/00247* (2013.01); *G01N 2035/00574* (2013.01); *Y10T 436/25* (2015.01)

(58) Field of Classification Search
CPC ............. G01R 33/302; G01R 33/1269; G01N 27/745; G01N 35/0098
USPC .................................... 422/552, 553; 436/526
See application file for complete search history.

(56) References Cited

U.S. PATENT DOCUMENTS

| | | | | |
|---|---|---|---|---|
| 5,686,271 | A * | 11/1997 | Mian et al. | 435/91.1 |
| 5,922,617 | A * | 7/1999 | Wang et al. | 436/518 |
| 6,355,491 | B1 * | 3/2002 | Zhou et al. | 436/518 |
| 7,351,376 | B1 * | 4/2008 | Quake et al. | 422/504 |
| 2002/0086443 | A1 * | 7/2002 | Bamdad | 436/526 |

\* cited by examiner

*Primary Examiner* — Jan Ludlow

(57) ABSTRACT

Chips that include one or more particle manipulation mechanisms, or force transduction elements, provided at specific locations to manipulate and localize particles proximal the substrate surface. In one embodiment, individually addressable magnetic control mechanisms such as electric coils are provided at specific locations to create a magnetic field to attract magnetic particles, such a magnetic or magnetizable beads, to those specific locations. In another embodiment, electrostatic control mechanisms such as electrodes are provided to attract and manipulate electrically charged microparticles. A location may include a crater or well formed in the substrate, or it may include an element on the surface of the substrate. In some embodiments, one or more sensors are located proximal specific locations, e.g., specific craters, so as to analyze specific conditions at each location. In other embodiments, multiple locations share one or more sensors.

20 Claims, 14 Drawing Sheets

Figure 14. Top view of a silicon surface with a doped region (region 2). The electric circuit is completed by Vpot. using two leads contacting each region.

*Figure 15. A crater from above, with a doped region (e.g., photodiode) on the bottom and also two circuits with capacitive detection capability on the sloping insides of the crater.*

SYSTEM AND METHODS FOR LOCALIZING AND ANALYZING SAMPLES ON A BIO-SENSOR CHIP

CROSS REFERENCE TO RELATED APPLICATIONS

This application is a continuation of U.S. Ser. No. 09/683,861, filed Feb. 22, 2002, now U.S. Pat. No. 7,998,746 which is a continuation-in-part of U.S. Ser. No. 09/963,866 (now abandoned), filed Sep. 26, 2001. which is a continuation of U.S. Ser. No. 09/938,471 (now abandoned), filed Aug. 23, 2001, which claims the benefit of U.S. Provisional Ser. No. 60/228,015, filed Aug. 24, 2000, each of which is hereby incorporated by reference in its entirety.

BACKGROUND OF INVENTION

1. Technical Field

The present invention relates generally to methods, systems and arrangements for manipulating, localizing and analyzing samples, and more particularly to systems, methods and device arrangements for manipulating, localizing and analyzing samples, such as chemically or biologically active species on micro-beads, on a bio-sensing device.

2. Background Information

There exists an enormous number of processes occurring in an organism over a given unit of time and also in each cell of the organism. One needs therefore fast techniques that enable acquisition of information about such processes in parallel, and effective means for storing and handling such information.

High throughput screening (HTS) examines in parallel very small sample amounts (so as not to use large amounts of expensive and rare chemicals) and as many of these as possible. The easiest and the most logical (from the point of view of information handling) way is to arrange such complex samples in dense, solid-phase matrix, often implemented on and referred to as a "chip".

One example of such preparation is given in FIG. 1 (Biophotonics, January/February 2000, Univ. of Wisconsin, Franco Cerrina, et al.). According to this technique, a matrix is created by burning away deposits from certain selected places on a chip, while depositing additional chemicals on other places. This method, although fairly fast and cheap, produces a permanent pattern on a matrix, which will be used up after a single experiment. Thus, each new experiment requires production of a new matrix.

The number of elements (spots or locations) in a matrix varies depending on the preparation method, but usually does not exceed 10,000, although matrices as large as 1,000,000 sites have been reported. The outcome of each single "experiment" therefore gives at best 10,000 results. In reality this number is much lower (around 20%) due to the very poor quality of even the best matrices produced to date.

Apart from preparation mentioned above a complete HTS-system should also include means of detection of the events taking place in each location as well as data transfer and processing capabilities.

Relevant art includes: FR 2,781,886; U.S. Pat. Nos. 5,874,219, 5,922,617, and 5,755,942; PCT applications WO 00/43534, WO 00/49382, WO 00/60356, and WO 00/54882, each of which is hereby incorporated by reference for all purposes.

It is desirable to provide systems and methods for manipulating, localizing and analyzing samples and related processes in an efficient and effective manner.

SUMMARY OF INVENTION

The present invention provides systems and methods for manipulating samples, localizing one or more samples at specific locations, and analyzing samples and related reactions and processes. More specifically, the present invention provides platforms, such as a biosensor chip including arrangements configured to manipulate and localize samples, such as chemically or biologically active species on micro-particles, and to analyze the samples and related reactions and processes.

The techniques of the present invention allow for numerous applications including, for example, creating combinatorial libraries of chemicals useful for rapid screening of new chemicals to be used as drugs, both with regard to their function and (importantly) with regard to the determination of the side effects that a given drug might exert. Additional applications include. DNA hybridization, genome determination, proteomics and others.

According to the present invention, a bio-sensing chip includes one or more particle Manipulation mechanisms, or force transduction elements, provided at specific locations to manipulate and localize particles proximal the substrate surface. For example, in one embodiment, individually addressable magnetic control mechanisms such as electric coils are provided at specific locations to create a magnetic field to attract magnetic particles, such a magnetic or magnetizable beads, to those specific locations. In another embodiment, electrostatic control mechanisms such as electrodes are provided to attract and manipulate electrically charged microparticles. A location may include a crater or well formed in the substrate, or it may include an element on the surface of the substrate. In some embodiments, one or more sensors are located proximal specific locations, e.g., specific craters, so as to analyze specific conditions at each location. In other embodiments, multiple locations share one or more sensors.

In embodiments including craters, micro-particles are localized within selected craters through selective activation of the corresponding control mechanisms. Larger micro-beads are provided in some embodiment to act as caps or lids for the craters. Other lids and lid actuation mechanisms are also provided, including, for example, individually addressable sliding doors and micro-shutters. Individually controllable lids allow for contained environments within each crater or well. By controlling the lids, each enclosed volume becomes separated from the surrounding environment. Any materials, e.g., fluid medium within an enclosed crater, particles suspended therein; and/or material that adheres to an enclosed crater's inner surface, are not affected by subsequent changes that occur in the surrounding environment while the lid is closed. A lid may or may not be completely liquid-tight, but mixing of the medium outside an enclosed well with the medium contained inside a well will be dramatically slowed. Hence, each lid provides an effective means to separate materials, e.g., solids and/or liquids, in the interior of the well from materials outside the enclosed well. In this manner, different wells can be populated with controlled amounts of different substances, e.g., different chemical compounds, by selectively opening and closing wells as changes are made to the surrounding environment.

The present invention advantageously provides a user with the ability to quickly and efficiently custom design an "experiment" as opposed to using a ready-to-use product which is generally very difficult to modify. The present invention provides an easy-to-handle platform, which may be used repeatedly and may be prepared in-house. Consequently, the present invention is not limited to the surface deposits as are the devices described above (see, e.g., FIG. 1), but allows sample preparation either by surface deposition (e.g., at the bottom or at the walls of a crater) or by utilizing liquid state reactions allowing reagent contained in the liquid trapped within each well by a cap to mix with reagents contained in the liquid above the craters by opening the "lids" (caps) at will.

According to the invention, a chip is provided with at least one particle control mechanism that allows for controllable generation of a particle control field responsive to a control signal, the control field being generated to localize at least one of a plurality of samples. Preferably, the control mechanism generates a magnetic or electric force transduction field (control field). In magnetic control field embodiments, the control mechanism preferably includes one or more coils made of an electrically conducting material, such as aluminum, and/or a magnetically active material. In electrical control field embodiments, the control mechanism preferably includes one or more electrodes made of conducting material.

According to one aspect of the invention, a device arrangement includes a cavity provided in a substrate and a lid for closing the cavity. Each cavity is surrounded by a control device that directs the lid using one or more external magnets that create magnetic fields counteracting the field created by material deposited around each cavity. The cavities are etched in a silicon surface and the lid is provided as a large magnetic particle, such as a magnetic bead, in the liquid. The particle is attracted to a predetermined cavity when the coil of that cavity is energized by electric current to Produce a magnetic field of spatial attraction. Alternately; the particle is directed onto a cavity using external magnets that create magnetic fields counteracting the field created by material deposited around each cavity. Before sealing off the cavity, samples may be attracted into the cavity. The sample's may include magnetic particles covered with appropriate chemical(s). In one embodiment, the arrangement is configured to detect the presence of a magnetic capping lid capping a cavity. In one embodiment, the capping is detected by detecting the change in inductance in the control circuit which produces the attractive magnetic field, whereby the bead acts like a magnetic yoke in a transformer, increasing the inductance. In other embodiments, for example, the capping is detected through decrease of electromagnetic radiation to a detector inside the cavity or by changes of capacitance between electrodes inside the cavity or near a cavity rim.

The arrangement is also preferably configured to detect changes of inductance when a magnetic particle passes through the opening into or out of a cavity, so as to help keep track of the number of particles in a well or crater. The capping control coils, or a secondary set of coils may be used. The indication is determined using the direction of externally controlled magnetic field, either by changing the direction of the electric current flowing through a coil or flipping an external magnet. Preferably, each particle (including lid particles) contains particular molecular coating, which may react with the fluid or other material in that cavity or with a coating adsorbed on the walls of the cavity.

The substrate can be made of silicon, Si, or of Si-compound, such as Si-oxide Si-nitride or Si-carbide, or combinations thereof, or a suitable polymer, such as polyethylene, polyethylene glycol, polyethylene oxide, fluorine containing a polymer (PTFE-Teflon), or silicon containing a polymer.

According to another aspect of the invention, an arrangement includes a member for generating acoustic waves and a control device on a substrate or carrier. The control device and member for generating acoustic waves are covered with an insulating layer. On the insulating layer, a combination of a receptor and a bead of a magnetizable material are attached. The combination of receptor-bead attenuate the acoustic wave stronger than receptors attached to the insulating layer. Preferably, the surface of the insulating layer is inert to receptors, and that the receptor-bead combination is attached to the surface by magnetic forces acting on the bead.

The invention also relates to a method of localizing samples. A device for generating a force transduction field is selectively activated to create such a field to attract one or more particles or samples to a corresponding location such as a location on the substrate surface or a crater or pocket in the substrate. The method also includes controlling a magnetic lid for closing a cavity, for example, by directing a bead onto a cavity using external magnets that create magnetic fields counteracting the field created by material deposited around the cavity, and attracting smaller magnetic particles into the cavity before sealing off the cavity. The method also includes detecting the presence of a capping lid capping a cavity, for example, by detecting the change in inductance in a control circuit which produces an attractive magnetic field, whereby the bead acts like a magnetic yoke in a transformer, increasing the inductance. Detection may also be performed by detecting a decrease of electromagnetic radiation to a detector inside the cavity or by detecting changes of capacitance between electrodes inside the cavity or near the cavity rim. The method also includes detecting changes of inductance when a magnetic particle passes through the opening into or out of a cavity, and determining the indication using the direction of externally controlled magnetic field, either by changing the direction of the electric current flowing through a coil or flipping an external magnetic.

Given a known number of samples in each cavity and a density of respective coatings, quantitative data on the number of reaction between the coating on a wall, of the cavity and the coating on a small sample is obtained by counting the number of samples.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF DRAWINGS

FIG. 6 further illustrates an example of a structure including multiple coils (2 shown) formed around the entire depth of a crater;

DETAILED DESCRIPTION

The present invention provides platforms useful for performing a variety of biological and chemical assays. In one embodiment of the present invention a substrate is provided with one or a plurality of wells or craters formed in the substrate. Individually controllable lids are provided in some embodiments to allow for contained environments within each crater or well. Such devices are intended to be used in a fluid medium, for example, submerged in a liquid, covered by a gel, or introduced to air or other gaseous environment. By controlling the lids, each enclosed crater volume becomes separated from the surrounding environment. Any materials, e.g., fluid medium within the crater, particles suspended therein, and/or material that adheres to an enclosed crater's inner surface, are not affected by subsequent changes that occur in the surrounding environment while the lid is closed. Such changes include presenting different chemical compositions to the surrounding fluid medium, irradiating the device or individual craters, or providing solid materials in the surrounding medium. A lid may or may not be completely liquid-tight, but mixing of the medium outside an enclosed well with the medium contained inside a well will be dramatically slowed. Hence, each lid provides an effective means to separate materials, e.g., solids and/or liquids, in the interior of the well from materials outside the enclosed well. In this manner, different wells can be populated with controlled amounts of different substances, e.g., different chemical species, by selectively opening and closing wells as changes are made to the surrounding environment.

In some embodiments, one or more sensors are located proximal each crater so as to analyze specific conditions within each crater. In other embodiments, multiple craters share one or more sensors. Such sensors may be embedded within the substrate proximal the craters using known MEMS and/or semiconductor processing techniques, or they may be attached to the substrate individually or as part of an attachment module. Each sensor provided preferably includes a connection (e.g., separate conductive lead) to a controller, e.g., controller 18 of FIG. 3, or a connection to an intermediate modular structure such as a separate control module that detachably connects to the main substrate. Examples of such sensors include, optical detection sensors, temperature sensors, pH sensors and others as will be described in more detail later. Generally, the choice of sensor depends on factors including type of signal to sense, manufacturability within the process(es) used to manufacture of overall Microsystems, operability and reliability in the target operating environment, and possible interactions with other components in the system.

Figure 1:
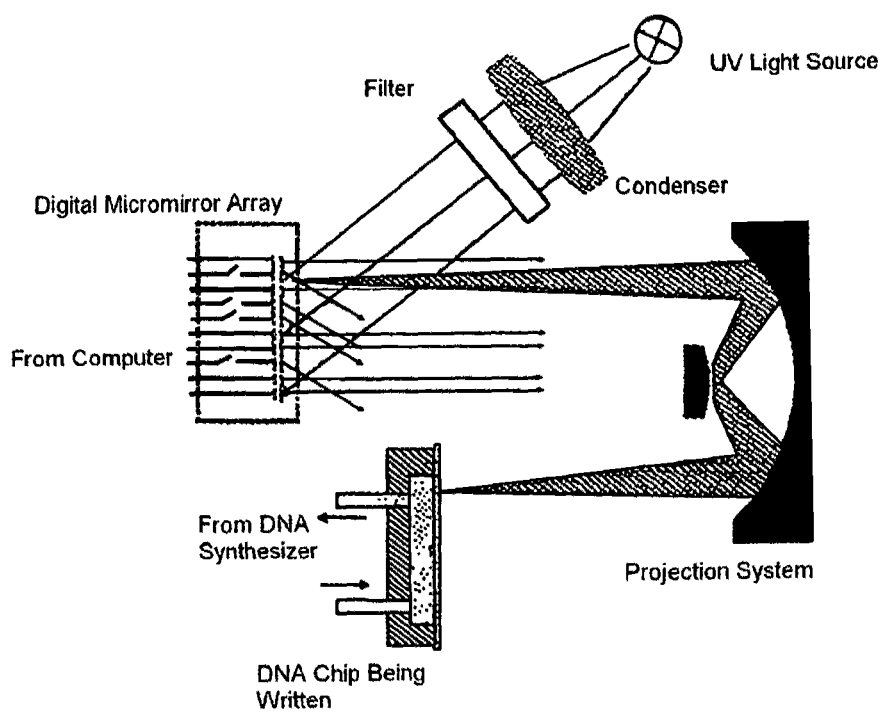
FIG. 1 shows an arrangement according to prior art.
Figure 2:
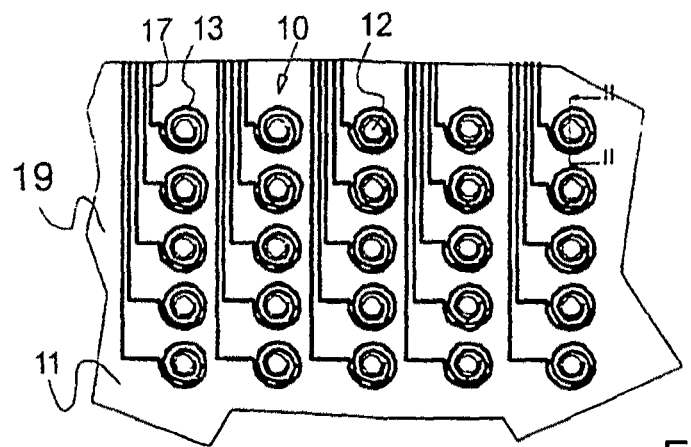
FIG. 2 is a schematic view from above of a chip according to the invention.
Figure 3:
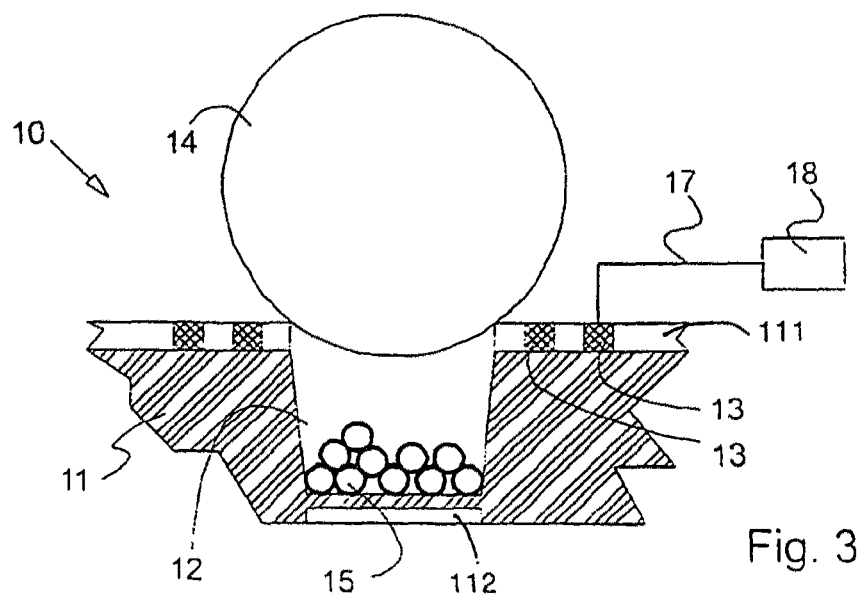
FIG. 3 is a schematic view, showing an enlarged, cross-section along line II-II through a part of the chip according to FIG. 2.

FIGS. 2 and 3 illustrate one embodiment of an arrangement according to the present invention. FIG. 2 illustrates an enlarged schematic view of a portion of a chip 19 including a plurality of sample collecting elements 10. As shown the sample collecting elements 10 are arranged in an ordered array, however, it should be appreciated that the element(s) 10 may be arranged in any fashion, ordered or unordered. Each sample collecting element 10 defines a specific location on the substrate 11 (e.g., a specific location on the surface of the substrate 11). Each sample collecting element 10 preferably includes a force transduction element 13 configured to produce a force sufficient to manipulate sample particles. In a preferred embodiment, each sample collecting element 10 includes a cavity (e.g., crater, pocket, well) 12 provided in a substrate 11 and a force transducing element 13. In some cavity embodiments, force transducing element 13 controls a cap mechanism, such as a lid 14 as shown in FIG. 3. Each force transducing element 13 is communicably coupled to a controller 18 via a communication path 17. Each communication path 17 preferably includes a conducting lead for providing electrical control and feedback signals between controller 18 and a force transducing element 13.

FIG. 3 is a schematic cross-section of a sample collecting element 10 on chip 19 in a state where samples 15 are collected in a crater 12, which is closed by means of the lid or closure element 14. The samples as shown are spherical particles, but it should be understood that the sample(s) may include any substance, solid, liquid, gel, etc. In a preferred embodiment, however, the samples 15 include one or more magnetic particles. In crater embodiments, each of the samples 15 preferably has a dimension, e.g., diameter, much smaller than that of the opening defined by the crater 12. The magnetic particles are preferably covered with desired chemical(s), biological materials, etc., appropriate for the desired assay.

In the embodiment shown in FIG. 3, the force transducing element 13 preferably includes one or more electrically actuated coils and the lid 14 includes a magnetizable bead. Lid actuation, i.e., closing and opening of each of the craters, is preferably performed using individually controllable magnetic fields that influence the motion of the introduced beads. Such magnetic fields are created by providing an electrical current to the coils 13 around each crater. Different lids and closure elements as well as modifications and other related aspects will be discussed in more detail below.

By making many craters 12, all with individually controlled lids 14, different types of mixing of solids dispensed in a liquid and/or liquids can be achieved at the same time. As different liquids/solids are introduced to the outside of the craters only user-selected craters with open lids will be exposed for the mixing by the liquid/solids external to the closed craters.

In the present embodiment, each crater 12 preferably has a circular cross-section (orthogonal to plane of FIG. 3) about 50 μm deep with a diameter of approximately 100 μm. The dimensions and the shapes of each crater 12 can of course vary within a large interval both with respect to its diameter and depth. For example, the craters can have circular cross-section with a depth of from about 1 μm to 50 μm to 100 μm or even more, and a diameter of approximately 10 μm to 100 μm or even greater. It is well known in the semiconductor processing and related arts to produce craters with dimensions ranging from a few μm and larger and with depth ranging from a few μm and up to several hundreds of μm, having, e.g. square shapes, spherical shapes, conical shapes, etc. Each crater 12 may also have an opening that is much smaller than the dimension of the main crater, e.g., a small opening or channel leading to a larger chamber. Additionally, multiple craters may open into a larger shared chamber.

The general idea of the present invention is to manipulate small particles in order to bring one or more to a specific location on the surface of the substrate using individually addressable magnetic field(s), or other force transduction fields, as a driving force for particle manipulation. The surface of the substrate may be either patterned in a particular manner, or not. When the substrate includes craters (with or without a pattern) as shown in FIG. 3, some particles may be used as caps or lids to close craters as described earlier. When the substrate is left without a pattern or patterned in a different manner the particles can be used mainly as a way to enhance sensitivity of detection of the processes taking place in the device (e.g., on the surface of the substrate).

Magnetic forces to manipulate the particles are created using coils as described above, but also may be created using externally applied magnets. In the former case the field strength (and thus the magnitude of the force) is determined primarily by the number of windings in the coil and the magnitude of the electric current. In the latter case it is possible to control the magnitude of the magnetic force by appropriate choice of magnet position and strength.

The material of the substrate is preferably silicon (Si) or a silicon-based compound, e.g. Si-oxide Si-nitride or Si-carbide, or combinations thereof. It may also include thin self-supporting Si, or of a Si-compound, with another film of suitable thickness (for example few micrometers), such as ZnO, evaporated onto its surface. Such as additional film is generally needed if the device is to work as an acoustic wave device for detection as will be discussed below. Additional materials, such as a suitable polymer, e.g. polyethylene, polyethylene glycol, polyethylene oxide, fluorine containing a polymer (PTFE, also known as Teflon®), or silicon containing a polymer, may be used as a substrate material.

When patterning the substrate, different techniques may be used depending on the substrate material and the pattern. The manufacturing process may include micro-machining and standard semiconductor processing techniques similar to the processes used to make microprocessors and memories chips. A device may contain anywhere from one specific location to several hundred specific locations to tens of thousands of specific locations or more on a single piece of silicon (e.g., from one crater to several hundred craters to tens of thousands of craters or more). Si and Si-compounds are suitably patterned applying well-known semiconductor processing techniques. When patterning polymers well known techniques such as polymer stamping or molding may be used.

Figure 4:
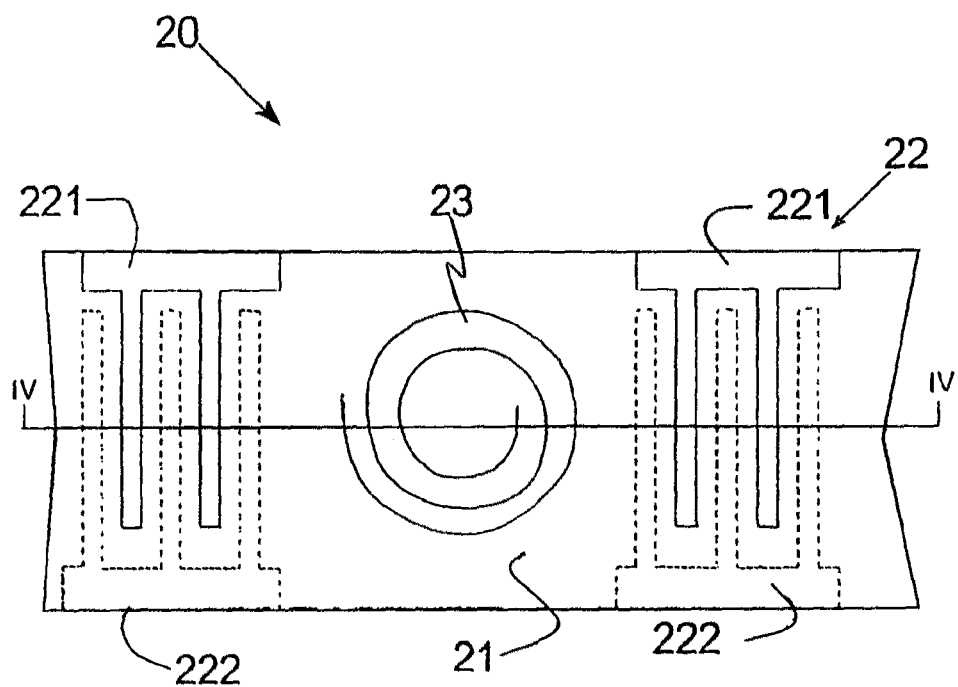
FIG. 4 is a schematic view from above of a part of another chip according to the invention.
Figure 5:
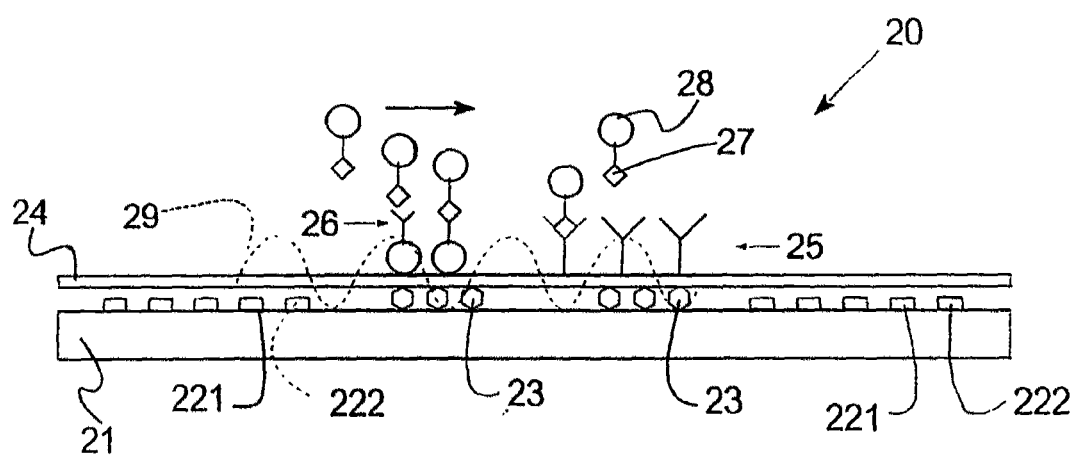
FIG. 5 is a schematic view, showing an enlarged cross-section along line IV-IV through a part of the chip according to FIG. 4.

The patterns on the substrate are not limited to sample collecting elements (e.g., force transduction elements 13 and/or craters). For example when using the device as an acoustic wave detector one may produce matrices including many interdigitated patterns needed for acoustic wave generation and detection. FIGS. 4 and 5 show one example of such a device capable of acoustic wave generation and detection as will be discussed later.

The coils 13 proximal each of the locations are preferably made of an electrically conducting material such as aluminum (Al), but any other electrical conductor may be used including copper (Cu), ITO, etc. The coils are preferably formed using well-known patterning techniques such as electroplating, chemical vapor deposition (CVD), sputtering, etc. Preferably, each coil is accessible through an electrically conducting lead 17 so that a current of desired strength can be individually applied to each coil. The strength of the resulting magnetic field is proportional to the current amplitude and the number of coil windings. Thus the strength of the magnetic field created by each force transduction element 13 can be varied by applying a current of desired amplitude. Additionally, an alternating current may be applied in those embodiments where an alternating field (e.g., alternating magnetic field) is desired. For example, an alternating field is desired to manipulate a magnetic bead in such a manner as to induce flow or mixing in the surrounding fluid. Further, different field strengths may be created at different locations, for example, by applying currents of different amplitude. Adjusting field strengths is useful to manipulate and re-localize samples. For example, materials localized at one location may be re-localized to a different location by adjusting the field strengths of adjacent regions and/or turning on and off the fields of adjacent regions so as to induce flow in a desired direction local to a particular region.

Figure 6:
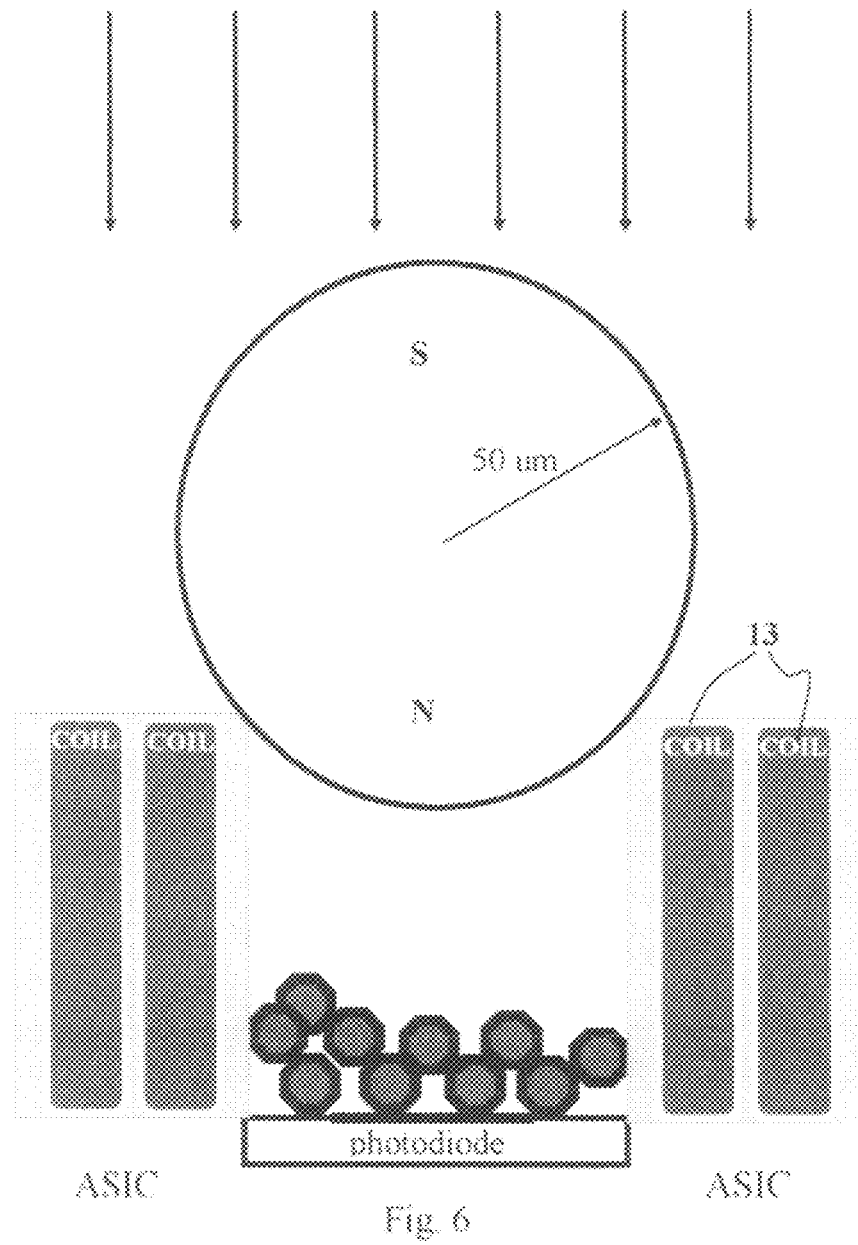
FIGS. 6 and 7 illustrate structures including photodiodes proximal the bottom of a crater and the walls/rim of a crater, respectively.

Clearly, it is possible to change the number of windings in the coils as well as their width and thickness within a broad range of dimensions. Preferably, the coils include from 2 and up to 10 or more windings. A single-winding coil, several multiple-winding coils, and other configurations are possible. Preferably, the coils are fabricated and operated such that the resulting field gradient is concentrated where particles should feel maximum force. The coils may also be formed in a layered structure, for example, with each subsequent coil layered on top of the next with insulating layers therebetween. Published PCT application WO 00/54882 discloses methods for forming such a layered coil structure, and is hereby incorporated by reference in its entirety. FIG. 6 illustrates an example of another useful structure wherein multiple coils 13 (2 shown) are formed around the entire depth of a crater.

In another embodiment, the force transduction mechanism includes a magnetically active material surrounding each crater. In this embodiment, magnetic particles and/or beads are manipulated using external magnets that create magnetic fields counteracting the field created by the magnetic material located proximal each crater 12.

Preferably, the craters are etched in the substrate surface and the lid is provided as a large (i.e., sufficient to close opening defined by crater 12) magnetic particle 14 in a liquid. Thus, particle 14 is attracted to a crater when an electric current is selectively applied to the coil(s) of the crater so as to produce a magnetic field. Before sealing off the crater of choice, however, it is also possible to attract smaller magnetic particles into the crater. To attract the smaller magnetic particles 15 to the crater, electric current is applied to the coil(s). When the coil is energized, a magnetic field is established, which attracts one or more magnetic particles 15 from the liquid. These smaller particles have higher mobility in the liquid compared to the mobility of larger particles and will thus typically reach the activated crater faster than a larger lid-particle. A large lid-particle will generally cap the crater after smaller particles have entered the crater due to the lower mobility of the larger particles. Methods for determining the number of particles and/or amount of material captured within a crater will be discussed later. Commercially available magnetic particles such as ferromagnetic or super-paramagnetic beads ranging in size from about 1 micrometer to about 100 micrometers in size or greater can be used. Generally, the size of the smaller (sample) particles should be much smaller than the size of the crater opening, and the size of the lid particles should be greater than the size of the opening. There are other dimensions and particle types on the market and the invention is applicable a broad range of particle sizes, shapes and materials.

In another embodiment, electrostatic force transduction mechanisms are provided. In this embodiment, particles desired to be manipulated preferably include an electric charge. In one embodiment, for example, a conducting plate or electrode may be positioned above a crater. An electric field can thus be created between the plate at one potential and an electrical conductor positioned proximal or within the crater and having a higher or lower potential, which field directs appropriately charged particles into or toward the crater. For example, an electric conducting ring, e.g., coils 13, and a plate above the crater can be used to create an electric field that can direct charged particles toward the crater. Alternately, a conducting plate positioned proximal the bottom of the crater can be used to create an electric field, either in conjunction with coils 13 or other conducting element positioned proximal the upper portion of the crater or with a conducting plate positioned above the crater. In yet another embodiment, only one electrode plate at one potential, e.g., at the bottom or side of a crater, is provided to attract a particle at another potential. For example the plate may be positively or negatively charged, and the particle(s) would be negatively or positively charged, respectively.

Preferably each electrostatic transduction mechanism is individually addressable, for example, one electrode element may connected to ground or other fixed potential, and in two electrode embodiments, the other electrode element is connected to a switch or similar circuit element used to selectively connect that element to a different potential.

In some embodiments, a horizontal (i.e., parallel to the surface of the substrate) field is applied using one or two sets of conducting plates, e.g., capacitors, so as to facilitate directed motion of charged particles, e.g., samples and lids, along the surface of the chip. For example, two large capacitors sandwiching the chip or a portion of the chip may be positioned orthogonal to each other so as to create orthogonal fields along the surface of the chip. Such fields may be used in conjunction with other force transduction fields.

Electric connections to the various electrode elements, e.g., plates, coils, etc., are implemented using various metals and bonding techniques as are well known. A non-conducting layer such as parylene, silicon nitride or other material is preferably implemented on the conducting electrode elements to electrically isolate the electrodes from the medium and charged particles.

Figure 8:
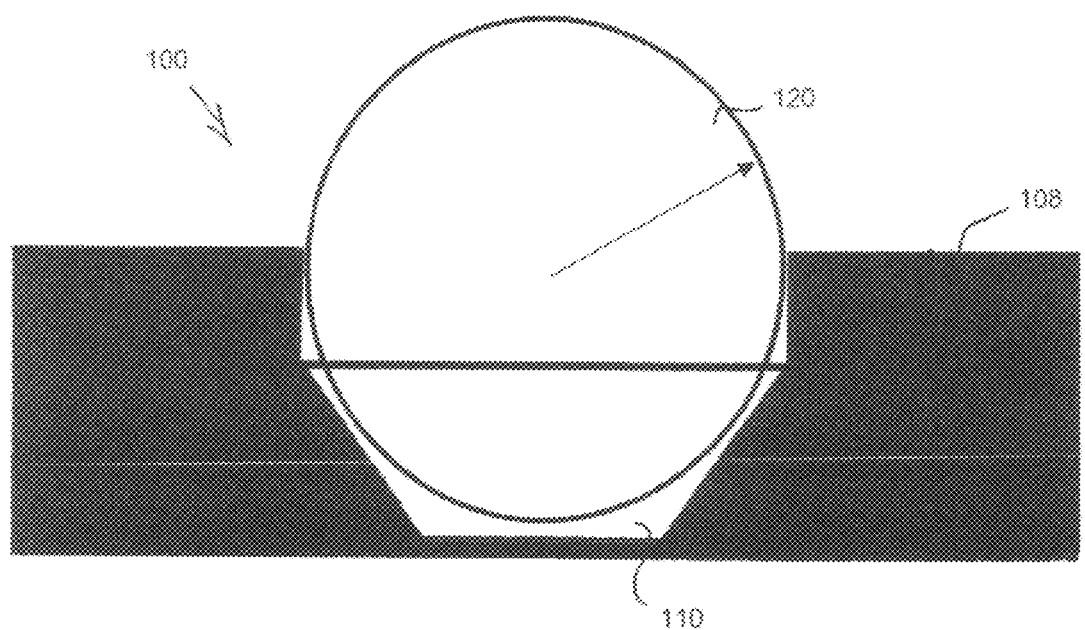
FIG. 8 illustrates such a structure including a crater or pocket substantially commensurate with the shape and size of a sample particle.

In one embodiment, the size of a crater is designed to be substantially commensurate with the shape and size of a sample particle, e.g., a capping particle or bead. FIG. 8 illustrates such a structure 100 including a crater or pocket substantially commensurate with the shape and size of a portion of a sample particle. As shown a substrate 108 includes a pocket 110 formed therein, e.g., via etching. Pocket 110 is substantially the same size and shape as bead 120. In one embodiment, one or more sensors 130 are positioned proximal pocket 110 as shown, for example, in FIGS. 9 and 10. Sensor(s) may include any type(s) of sensor(s) as desired for the particular assay(s), e.g., radiation sensors, pH sensors, etc. Sensor types and integration issues will be discussed below. In some embodiments, the pocket 110 is etched in or drilled into a sensor 130. The pocket 130 need not be in the active chip material. For example, a pocket could be on an overlay, a coating, in a cartridge or insert placed over a sensor system or substrate, etc. Preferably the particles or beads are introduced in a fluid medium. The beads may be introduced by flowing beads over the chip, by dipping the chip into a bead-containing sample, etc.

Figure 11:
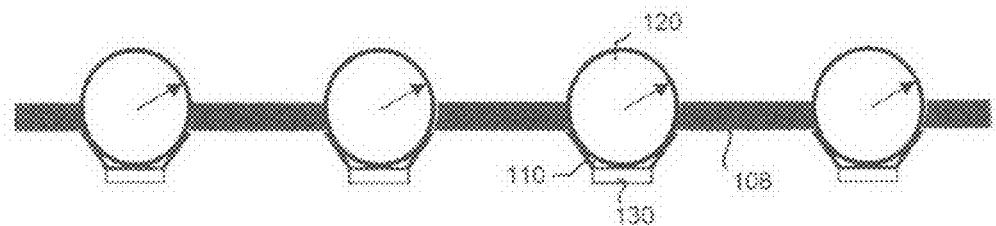
FIG. 11 illustrates an array of pocket structures formed on a substrate.

FIG. 11 illustrates an array of such pocket structures 100 formed on a substrate. The array may be ordered or it may be un-ordered. The density of pocket structure locations is limited only by the processes used to form the pockets. In embodiments including one or more sensors dedicated for each pocket, the density is limited only by the possible density of an array of sensor components.

Advantageously, the present embodiment provides dedicated real-time sensors for each particle or bead in each pocket 110. Further, although magnetic and/or electrostatic field generating transducers, e.g., coils, electrodes, etc., may be used to localize beads 120 in the pockets 110, such forces are advantageously not required in this embodiment.

Figure 12:
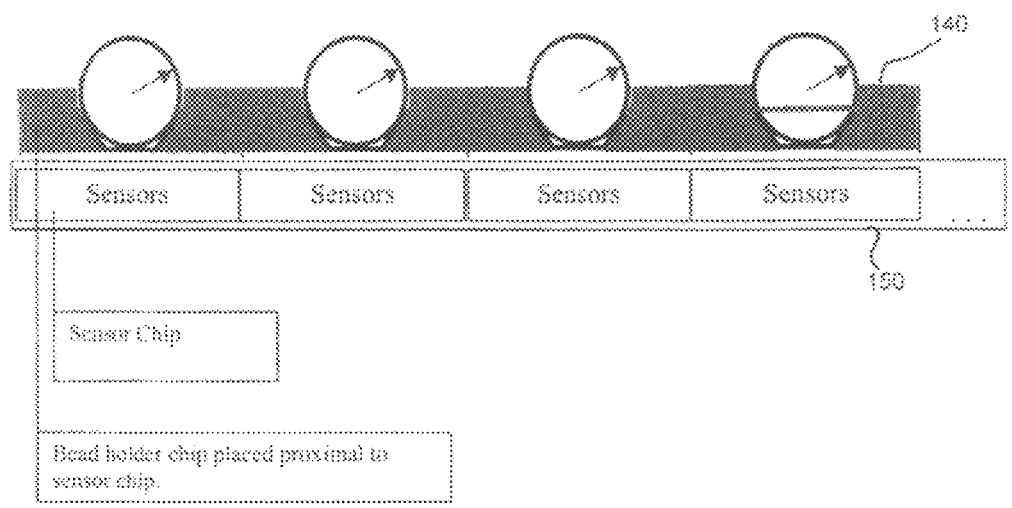
FIG. 12 illustrates a modular design including a pocket chip having an array of pocket structures, and a sensor chip including a complementary array of sensors.

FIG. 12 illustrates a modular design including a pocket chip 140 having an array of pocket structures, and a sensor chip 150 including a complementary array of sensors. On such useful sensor chip is a CMOS photodiode array. CMOS optical sensor chips are readily available, for example, as integrated in Intel's QX3 microscope, or sensors found in standard digital cameras. CCDs are also readily available. The density of pocket locations is limited only by the manufacturing processes and the density of the sensing elements on the selected sensing array. Preferably, the number of sensors is proportional to the number of pockets. For example, two to four photo-diodes of different color sensitivities can be associated with each pocket, or ten to one hundred pockets holding micron-sized beads over one sensor may be implemented. Of course, pockets need not be on a flat substrate. In some embodiments, pockets, craters, or other location-elements can be manufactured on substrates comprising an array of passive optical elements, such as an array of micro-lenses, or a composite array of fibers, that shape, filter, focus, or otherwise prepare or deliver a signal from the location-element to a sensor.

Figure 13:
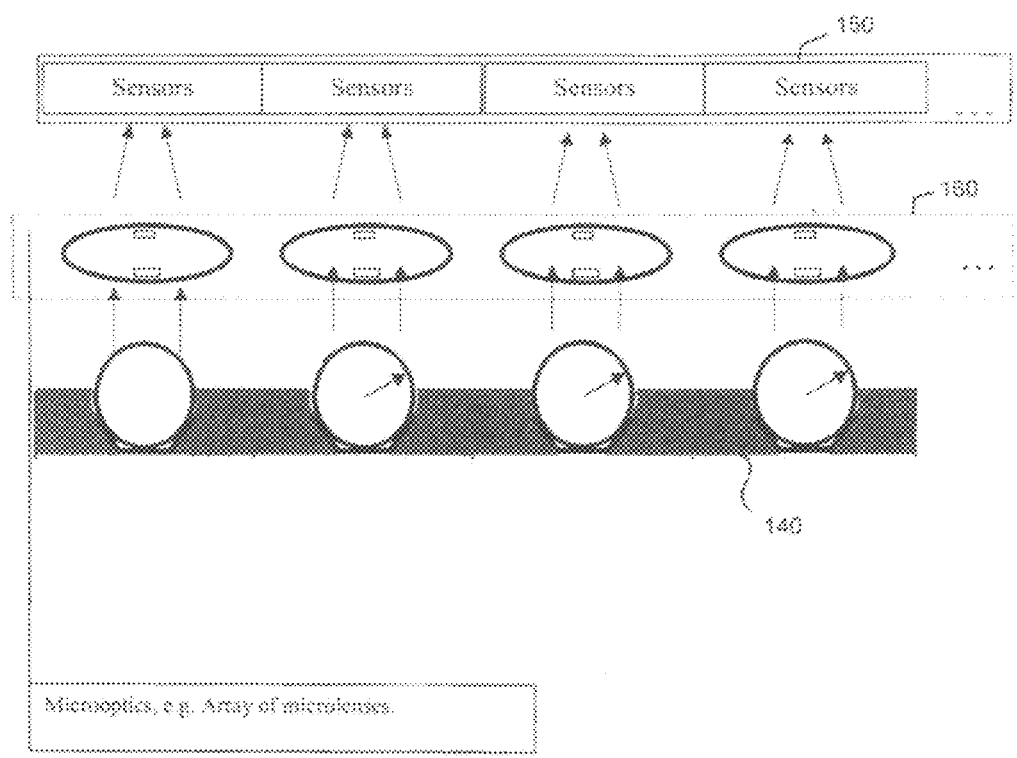
FIG. 13 illustrates a modular arrangement similar to the arrangement shown in FIG. 12, including an additional interface module including micro-optics.

FIG. 13 illustrates a modular arrangement similar to the arrangement shown in FIG. 12, including an additional interface module 160 including micro-optics, such as an array of micro-lenses, to enhance detection by the sensor array 150.

To open a closed crater, or a filled pocket, a repelling field is generated either externally or by inverting the direction of the current flowing through the coils. It is also possible to terminate the current through the coil, whereby the particle may be released due to shear force from a flowing fluid or due to gravitational forces, e.g., if the craters are positioned "upside down". In pocket embodiments, controlled release and retention of beads may be facilitated by introducing an appropriate bead transducing field, e.g., coils to produce a magnetic field. Electrostatic and/or electrowetting field transducing means may also be implemented. Also, a physical armature may be provided proximal each bead retaining pocket.

The simple actuation of the crater lid using current-controlled magnetic field(s) and the potentially large number of craters on a chip makes it desirable that the chip is operated automatically through a controlling arrangement. The chip is preferably provided with an interface device that establishes electrical connection with the chip and provides control of the handling of the surrounding fluid with the beads and chemicals. After use the chip may be removed for cleaning and reuse or disposal. The interface device is preferably configured to connect to a computer equipped with suitable software to control the sequence of operations on the craters and the liquid handling system. The software also preferably provides an interface (e.g., GUI) for the user to establish process sequences and to plan the states of the crater lids at each stage in each sequence.

In one embodiment, detection of a magnetic capping bead is performed. It is important to obtain feedback on which craters are capped, or which pockets are filled. The presence of a magnetic capping bead, in place over a crater or pocket, can be detected by the change in inductance in the electric circuit that produces the attractive magnetic field. A capping bead acts like a magnetic yoke in a transformer, increasing the inductance of the corresponding coil/circuit. Thus, a resonant, or other, circuit is provided to detect such an inductance change. One or more such resonance sensing circuits are preferably coupled to each lead 17. The presence of the capping bead can be detected using other various schemes, including, for example, detecting a decrease of electromagnetic radiation provided to a detector inside the crater or by detecting a change of capacitance between electrodes located inside the crater or near the crater rim.

Such induction detecting techniques are also useful for detecting when one or more small magnetic particles passes through the opening into a well. Using the arrangement according to the invention it is possible to determine whether a sphere is entering or leaving the well by detecting changes in inductance of coils 13. The direction is determined based on the polarity of the controlled magnetic field (either by changing the direction of the electric current flowing through a coil or flipping an external magnetic field creating device or by other means). Such a sphere may contain particular molecular coating, which will react with the liquid in that well or with a coating adsorbed on the walls of the crater. Given that one can determine the number of spheres in each well and the density of the respective coatings, quantitative data on the reactions occurring can be facilitated by counting the spheres. In one embodiment, a secondary set of coils is provided to detect particles entering or leaving a well. For example, the secondary set of coils may be positioned below the main coils 13 proximal the walls of the crater the secondary coils are preferably individually addressable and coupled via separate leads to a controller device.

The Following Non-Limiting Application Examples are Given for Enhancing the Understanding of the Invention:

According to a first example, liquid A containing magnetic beads is introduced to the surface of a chip including an array of craters. User selected craters 12 are energized and hence capped. The remaining beads are flushed away with a cleaning liquid. Now liquid B is introduced, containing small (much smaller than the capping beads) particles, called X, made of a material interesting to the user. Only uncapped craters will accept X. Then, more magnetic capping beads are introduced and selected craters are capped, trapping X. Cleaning liquid is used to flush all excess away. A liquid containing chemical reagent Y is then introduced and some craters are selectively opened. X and Y are allowed to mix and react, but only in the user selected areas. This reaction can be followed using sensing techniques, for example using optical techniques. Other detection techniques easily incorporated into the present embodiment are mentioned below.

In a second example, a substance is attached (e.g., deposited) to the craters inner surface. In a repeating sequence some craters are closed by capping beads and the others are exposed to a reactive chemical A. After the reaction the chemical is flushed and some craters are exposed to another chemical B. So there will be craters that have been exposed to A and B, some to A, some to B, and some to neither. This process can be repeated with many chemicals producing very large numbers of differently modified substances residing in different locations (craters) of choice. With a sequence of 10 different chemicals, for example, more than 1,000 different combinations may be obtained. In particular, this process could be used to synthesize DNA strands or (using appropriate well-known techniques) to investigate the functions of different proteins.

Yet another application is to lock cells or other biological material in wells filled with different chemicals and monitor the reaction of cells (cell proliferation, differentiation, spreading or others) to these chemistries. This would enable, for example, a fast, high-throughput drug-screening assay to be performed.

Devices and arrangements according to the present invention may also be used, for example, to deliver a certain chemical or chemicals locally at a certain place or places in a reaction vessel, and monitor reaction products locally, or to deliver a drug inside a body.

Another field of applications for the devices of the present invention is "low throughput screening" (LTS). LTS is often used when the amount of required information is smaller but in addition one wants to obtain some quantitative information about concentrations of analyses or number of reactions that occur during a certain time at certain amounts of reagents. An "electronic tongue", which is a device that enables one to determine components in a fluid, is an example of an LTS-type device. Components of a fluid can be associated with certain tastes (sweet, sour, salt, etc., or combinations thereof). To determine the content of simple liquids in a liquid mixture, for example, the % of sugar dissolved in a cup of tea along with the amount of tea used to prepare this cup, and even perhaps different tea blends used, requires performing several experiments with constituents that react differently to different tea blends and to different amounts of tea from each blend that has been used, as well as to the amounts of sugar being dissolved in the tea. Such LTS methods can be performed using the present invention by choosing appropriate reagents different for each crater and letting these first react with "standard" samples (calibrating or "learning the tongue" to recognize certain non-mixed liquids) and later exposing these samples to mixtures of different tea blends with or without sugar. Appropriate data processing, e.g., comparing the results with the calibrated values obtained on standard samples, enables one to obtain information about tea blends used and the amount of sugar dissolved.

SAW Device Application

A single site of a matrix of a piezoelectric Surface Acoustic Wave, SAW, device is shown in FIGS. 4 and 5. Each device 20, includes an arrangement 22 for generating acoustic waves and one or more magnetic field control mechanisms 23 (one shown) on a substrate or carrier 21. The arrangement for generation and detection of acoustic waves includes two finger-shaped, reversed arranged conductors 221 and 222 provided on both sides of the control mechanism 23. One of the conductors acts as the wave generator and the other acts as the wave detector. The control mechanism 23 is arranged as a coil connected to a controller (not shown) as described in conjunction with foregoing embodiments. The coil and the arrangement for generating acoustic waves are covered with an insulating layer 24 (FIG. 5), made of, e.g., glass or plastic, or a biomolecular layer. Onto this insulating layer, (biomolecular) "receptors" 25 may be adsorbed. The receptors 25 can be used in their native state and adsorbed spontaneously onto a suitably prepared insulating layer 24. The receptors may also be pre-adsorbed onto small magnetic beads 28 and the whole complex (magnetic bead-receptor) can be attracted to the surface of the SAW-device by magnetic field created by passing a current through the coil 23. The beads+ receptors attenuate the acoustic waves 29 many times stronger compared to the case when native receptors are attached to the insulating layer 24, and thus much lower concentrations of adsorbates at the surface are needed when the receptor-bead complexes are adsorbed.

Another advantage of such configuration is that it allows for the regeneration of the device. It is possible to manufacture the surface of the insulating layer 24 inert to receptors themselves, so that the receptor and bead complex is attached to the surface by magnetic forces acting on a bead. Once the investigation is completed the magnetic field can be removed (or the direction of the field changed using external magnet) causing the receptor and bead complex to desorb. This will leave the surface in its as-prepared state ready for another investigation.

If one wishes to study the reaction between these receptors and appropriate "donors" 27, the latter may be introduced in their native stage 27, or coupled to a magnetic bead 28.

Again, coupling the donors to magnetic beads allows for larger attenuation of acoustic waves when the acceptor-donor reaction has occurred (irrespective from whether this reaction caused additional donor-derived beads to be adsorbed on the surface or whether it caused the desorption of the reaction product—receptor+ bead/donor+ bead) which decreases the necessary number of reaction needed for a given sensitivity of the device.

Since the beads influence the propagation of acoustic waves more so than do the molecules which react to each other one obtains many-fold enhancement of the detection of the chemical reaction involving these molecules. One particular example of such reaction is the antibody-antigen reaction. Another example would be DNA—complementary DNA (or PNA) reaction. The reaction may occur spontaneously over many sites of the matrix, leaving other sites unreacted. By separately applying the magnetic field so as to remove particles from each site one obtains (i) a pattern over sites where reaction did take place, and (ii) a quantitative information about the number of reaction that did take place at each site.

Another use of the interdigited electrodes of such a matrix is as a capacitor; a certain number of electrode pairs will be considered as a single site and will constitute a capacitor. Each site of the matrix may be prepared differently, e.g., using different chemistries. By directing beads, with specific molecules attached to them, to these sites using magnetic fields, or other force transduction fields, or withdrawing particles from these sites, one is able to perturb the dielectric constant of a layer close to the surface and therefore produce detectable changes of the capacitance of the device compared to attachment of only (bio)molecules.

Lid/Closure Element Types and Related Aspects

Although lids as described in the above embodiments are preferably substantially spherical particles, such as microbeads, it should be appreciated that many other types of particles and closure elements may be implemented.

For example, the field of microshutters teaches many forms of covers for blocking light, such as in uses for optical cameras and astronomy equipment. One of ordinary skill will appreciate many individually addressable microshutters, comb drive mechanisms, lateral motors, micro-valves, and other micro-components or systems can be adapted to provide lids for the present invention. Cover elements that can be used as lids, include flaps or elements that bend or change curvature or roll or unroll; elements that slide horizontally to cover an opening; elements that pivot about an axis to cover an opening; hinged or swinging elements that swing to cover an opening; liquids or polymers that alter shape to cover an opening of liquid, such as ferrofluids or gels or polymers, electro- or magneto-rheological fluids or gels or polymers, with molecules optionally adsorbed or covalently tethered proximal to an opening; systems including controlled presence of discrete portions and forms of fluid (e.g., Agilent's Photonic Switching Platform) or electrowetting systems or plates (e.g., Nanolytics), and others. Mobile elements, such as rigid pop-up panels or sliding shutters, provide for a mechanism to substantially inhibit passage through an opening by diverting or blocking flow or flux through an opening. Grooved, patterned, treated, and other types of complex lids are possible.

A lid may include many of the materials that may also comprise an opening. For example, a lid may include a flat element comprising a mobile grating that slides or moves across openings. Generally, one or more openings can be simultaneously covered by such a lid, and a lid can be interposed between an opening and the environment but still allow passage through the lid and thereby exposing an opening to its environment. Additionally, a lid particle can have grooves, holes, flat areas, curved areas, cracks, and other physical features enabling controllable or selective passage. Other particle shapes include ball cones; cones; cut slugs; diagonals; eclipses; pins; pyramids; crystalline or combined crystal shapes; rods; ellipsoids or semi-spherical shapes; partial spheres, notched spheres, or hemi-spheres; squashed shapes; teardrops; bullets; cubes, parallelepipeds, trapezoids, or other geometric shapes; needles; shells, partial shells, or partially filled shells of other shapes; tubes; molecular shapes including fullerene-like shapes; composite shapes and materials such as layered shapes; discs; or other shapes or irregular versions of shapes. Particles may be joined versions of other particles; be notched or modified; rough, smooth, patterned; with or without one or more holes, cracks; branched or unbranched; extended or compact; symmetric or asymmetric in a given axis or aspect; layered or unlayered; heterogeneous or homogenous in composition; or otherwise manufactured or micromachined as appropriate for a given device, or a given use such as to comprise a lid, particle-in-a-well, or other aspects of the present invention. Particles may include or be associated with other compositions, for example cells with or without magnetic material or net charge, or agglomerations or functioning complexes of biopolymers or macromolecules including those including a magnetic or magnetizable material or charge.

As used herein particle, bead, closure element and lid should generally be held interchangeably herein. Examples of surface chemistry, size, geometry, etc., of particles, beads, lids, are often applicable to each of these terms in different situations.

An opening can be positioned in many ways with respect to a lid, and openings proximal to a larger surface can be positioned in a wide variety of ways in addition to being substantially parallel to that surface. For example, an opening can be on an incline, in the side of a vertical surface, on a rough or patterned surface, on the under-side of a surface, or/and many other places where an opening can be fabricated. An opening need not be a single aperture, or devoid of solid material. For example, an opening can comprise a collection of smaller, similar sized, or larger openings, or semi-permeable or selectively transparent composition. Examples include openings that comprise a grating, mesh, membrane, filter, gel, porous material, resins or materials such as those used in chromatography or purification, or other composition permitting passage. Openings may also comprise channels, etchings, grooves, capillaries, depressions, or other structures. Combinations of structures or simpler openings, such as their intersections, crossings, parallel or aligned placement with a region of mutual proximity, and other arrangements are contemplated.

Flow or passage of material across or near a surface, such as surface-layer laminar flow, can be affected by interposition, non-interposition, placement, motion or proximity of an appropriate lid, particle, or sample. Micromixing, for example, is achieved by repeated or controlled motion of lids, particles, samples, or other materials whose localization is influenced by the transducer elements of the present invention.

In many situations, the area of closure is related to passage of material through regions interposed by lids, rather than through openings proximal to the lids. For example, a lid casting a shadow over an area can alter the access of light or other material to that area. Lids can selectively shield areas, for example, to control deposition of materials or chemical alteration in processes like lithography, photo-chemistry, vapor deposition or spraying, or other deposition or treatment methods affected by accessibility controlled by lids.

Lids may control access to portions of lids. For example, where a lid isolates a cavity from the surrounding environment, a portion of the lid is also isolated from the environment. Additionally, the portion of a particle placed over an opening may be subject to differential environments based on a portion being over the opening, near the opening, distant from the opening, etc. Further, lids and portions of lids are subject to treatment, modification, chemical manipulation, and many other processes, treatments, and methods such as those provided herein.

It should be appreciated that lids may be modified, treated, altered, and otherwise used in many ways as tools for manipulating samples, preparing samples, and so forth. Lids may, for example, be used similar to paddles or stirrers to induce fluid motion or achieve micromixing. Lids, or elements controlling or sensing the motion of lids or other particles or materials, may be operated individually or in a fashion coordinating the operation of a plurality of lids. A plurality of lids may be substantially similar in some characteristics, or substantially different in others. It should be appreciated that chemical processes and treatments applicable to other components of the invention are applicable to lids.

One aspect of the present invention is to allow one to "mimic" or duplicate conditions and situations that are readily used with other well-understood methods, protocols, conditions, etc. in a particular field of art, and thereby facilitate the use of the present invention in fields of art where said conditions are readily understood, including fields of art where the processes, materials, conditions, and compositions of micro-fabrication are difficult to apply or not commonly used. In one aspect, mimicking conditions, chemical surfaces, etc. enables one of ordinary skill to apply the present invention to use in, or readily adapt prior art techniques for device preparation to, the micro-scale world. For example, a biochip surface, lids, or other components of the present invention can be fabricated to expose standard chemical functional groups, such as those found in silanized glass-ware or plastic sample tubes. Workers of ordinary skill in biology and chemistry, for example, are familiar with many shapes, forms, and compositions having surfaces similar to those in laboratory glass-ware or test-tubes, and should readily appreciate the many surface coatings, treatments, measurements, protocols, and other situations where a device with a standard molecular surface, be it a micro or other device, may be used. Properties other than surface chemistry may also be incorporated to leverage prior art knowledge, materials, and techniques. For example, depth-dependent aspects compatible with standard conditions in a field of use may be implemented, such as including an appropriate gold-coated surface or diffraction grating into portions of the devices of the present invention for use with surface plasmon resonance measurement techniques.

Lids, particles, substrates, and other material components of the present invention can have surfaces that are convenient for manufacture, processing, use, or adaptation of existing methods. These surfaces can be substantially similar at the molecular or chemical level. One, several, or all of the components of the devices of the present invention can have outer layers or coatings that are at some point substantially similar. A chip or device of the present invention and lids can have similar surface chemistries, such as chemistries similar to silanized glassware commonly used in molecular biology protocols. In such an example, both the chip and lids could be treated with a wide variety of coatings and processes known as useful in molecular biology for creating surfaces compatible with biological or chemical reactions and samples.

One skilled in the art should readily appreciate possible manufacturing, environmental, and reliability issues and solutions associated with the present invention. Lids of significant contact area with a substrate, for example, can be subject to manufacturing considerations such as high stiction forces, damage during de-wetting or manufacture involving liquid steps or capillary forces, particulate contamination, environmental degradation, etc. Stiction forces between lids may be moderated for efficient use. Anti-stiction techniques, such as using anti-stiction or low-friction materials, applying coatings including low-surface-energy fluorinated hydrocarbons or self-assembled monolayers, incorporation of textured surfaces or posts, and other known methods can be used implemented. Relevant references include Mastrangelo, C H. *Suppression of Stiction in MEMS*, and Maboudian, Roya. *Surface processes in MEMS technology*, Surface Science Reports 30 (1998) 207-269, both of which are hereby incorporated by reference.

Some environments, use in a conducting environment or liquid being one example, may require electrical or chemical isolation of components such as microshutters that would otherwise inappropriately expose conducting materials or materials corroded or adversely affected by their placement or operation in said environment. Coatings for electrical isolation or chemical protection of sensitive substrates may be used in adapting micro-device or closure mechanisms. Many anti-stiction or conformal coatings, provide low conductivity, chemical or environmental protection, and other appropriate properties appreciated and understood by one of ordinary skill. Micro-components, for example particular lids and lid-closure systems or particular force transduction systems, that may be used in one environment, such as gas-phase usage for controlling passage of spray material through an opening, but not another environment, such as isolation of proteins from dyes or chemicals in a nearby aqueous environment, should be readily apparent to one skilled in the art. For example, substituting a magnetic coil transduction system, or other transduction system for an electrostatic force transduction system in environments where the electrostatics are inappropriate, inadequate, or have undesirable side effects due charged materials in surrounding environment should be readily appreciated. Environments with high ionic strength or electrostatic shielding, for example, can interfere with the effect of an electrostatic attraction or repulsion in a force-transducing element. Magnetic elements are generally less subject to shielding in such conditions and would thus be appreciated as a replacement for the electrostatic force-transducing element when advantageous.

Lids may operate differently with respect to passage in different directions through an opening. For example, in situations where pressure pushes a lid away from an opening, or towards an opening, the lid may be more or less easily moved or disposed to allow passage. As an example, in a flap or particle forming a lid over a hole or crater, material exerting pressure from inside the hole could push past the particle or flap, or pressure from outside the hole could push the lid onto the hole more tightly. To expand upon this example, pressure outside the hole could push and move the lid such that the lid buckles, compresses, or changes shape, or the moves the lid past a notch or opening or other feature, such that under particular high or low or other pressure conditions passage would be increased somewhat similar to a safety-valve result. More generally, one-way passage, selective passage, condition-dependent or material-dependent passage may be achieved using the teachings of the present invention.

Sensor Integration and Other Aspects

Figure 7:
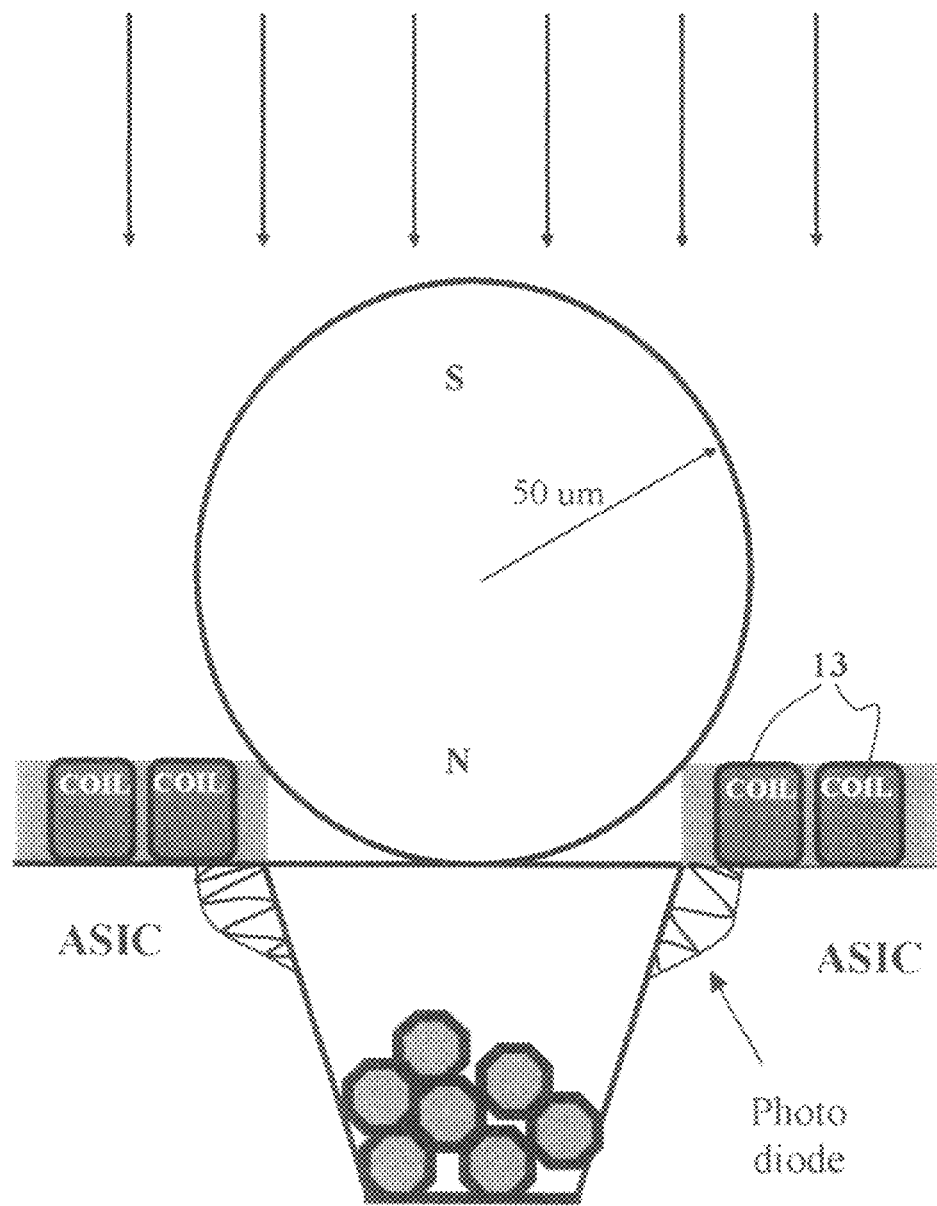
Figure 9:
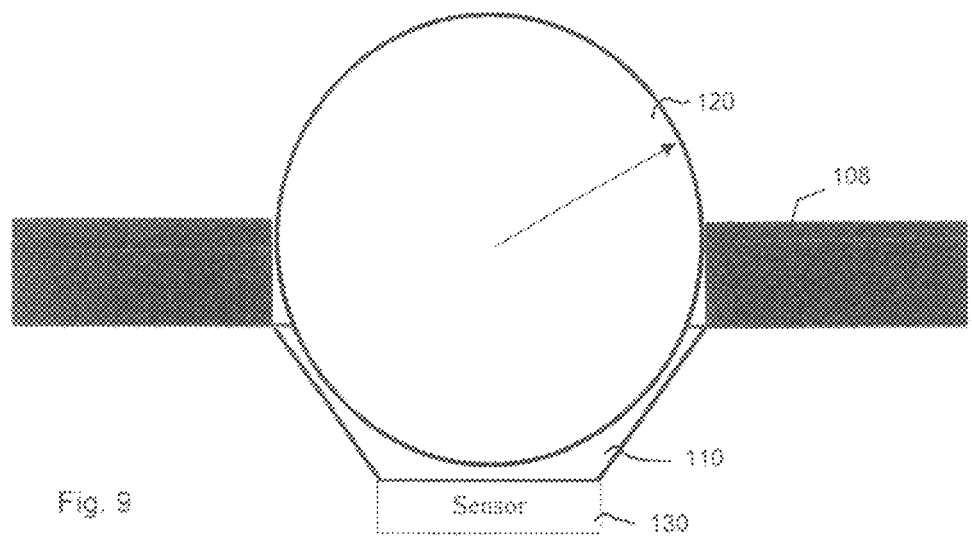
FIGS. 9 and 10 illustrate the structure of FIG. 8, including one or more sensors positioned proximal a pocket.
Figure 10:
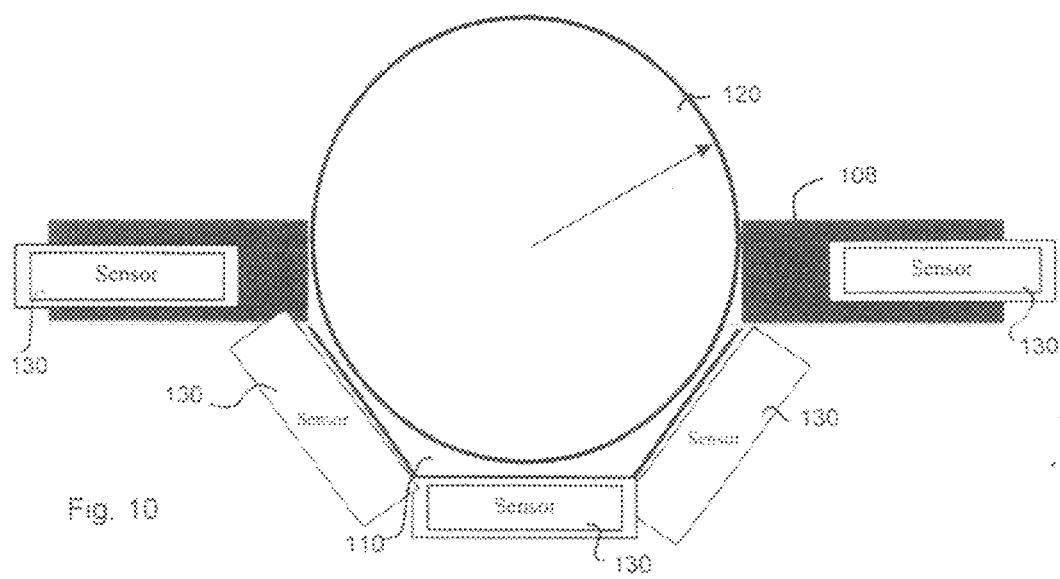

The microsystem platforms provided herein allow for the integration of a broad range of microsensors, transducers, and micro-components. For example, a photodiode may be placed proximal each location (e.g., under a location on the substrate surface, or on or under the bottom of a crater, or on or in the walls of a crater) and used to monitor the phosphorescent, chemiluminescent, fluorescent or other optical signals of molecules near that sensor. If the location includes a cavity with closed lid, the photodiode enables measurement of the optical signals emitted by one or more samples isolated in the cavity. FIGS. 6 and 7 illustrate embodiments including photodiodes proximal the bottom of a crater and the walls/rim of a crater, respectively. FIGS. 8 and 9 illustrate additional sensor configurations useful for crater embodiments. It should be appreciated that photodiode elements in FIGS. 6 and 7 may be replaced or supplemented with other sensor types desired for the particular assay as discussed herein. In preferred aspects, all detectors and sensors should be covered by an inert, transparent, layer to electrically, biologically, and chemically isolate them from the fluid medium and/or samples in the surrounding environment.

According to one embodiment of the present invention, a photo detector includes the interface between two doped regions of silicon. Often the bulk of a silicone chip is pre-doped, and by doping a limited chip area differently, the interface between the two active regions is obtained. The main issue is often to contact the two regions with metal conductors, which in turn can close the circuit electrically. Assuming the bulk is doped, the second region can be doped on the bottom of a crater, on the side of a crater or around the crater. The light from or to the crater, however, must be able to penetrate the doped region and reach the interface. This is easily achieved on the bottom of the crater.

Figure 14:
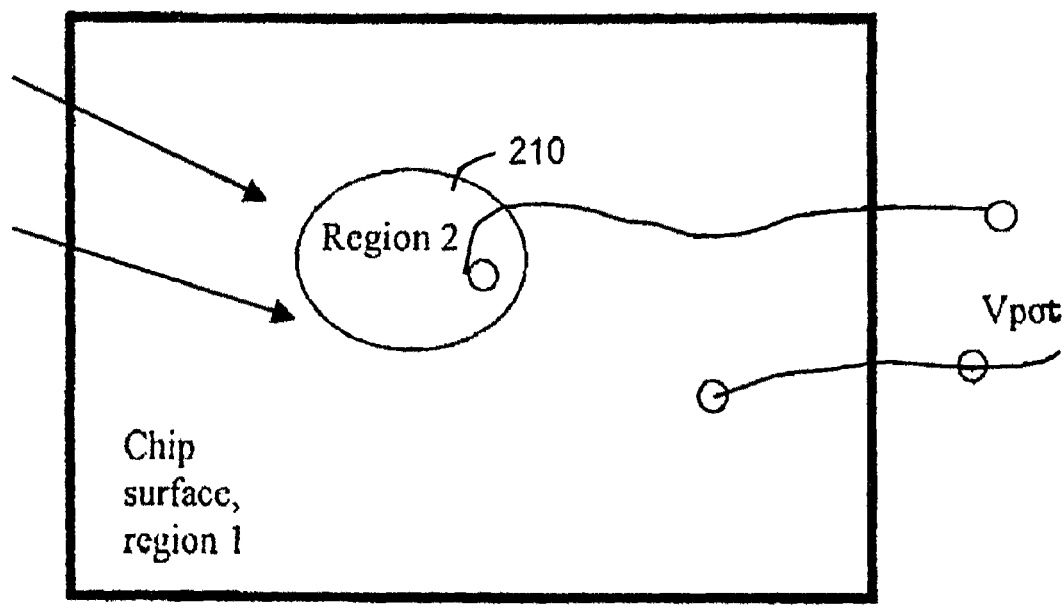
FIG. 14 illustrates a silicon surface including two regions of different doping useful for forming a photo detector.
Figure 16:
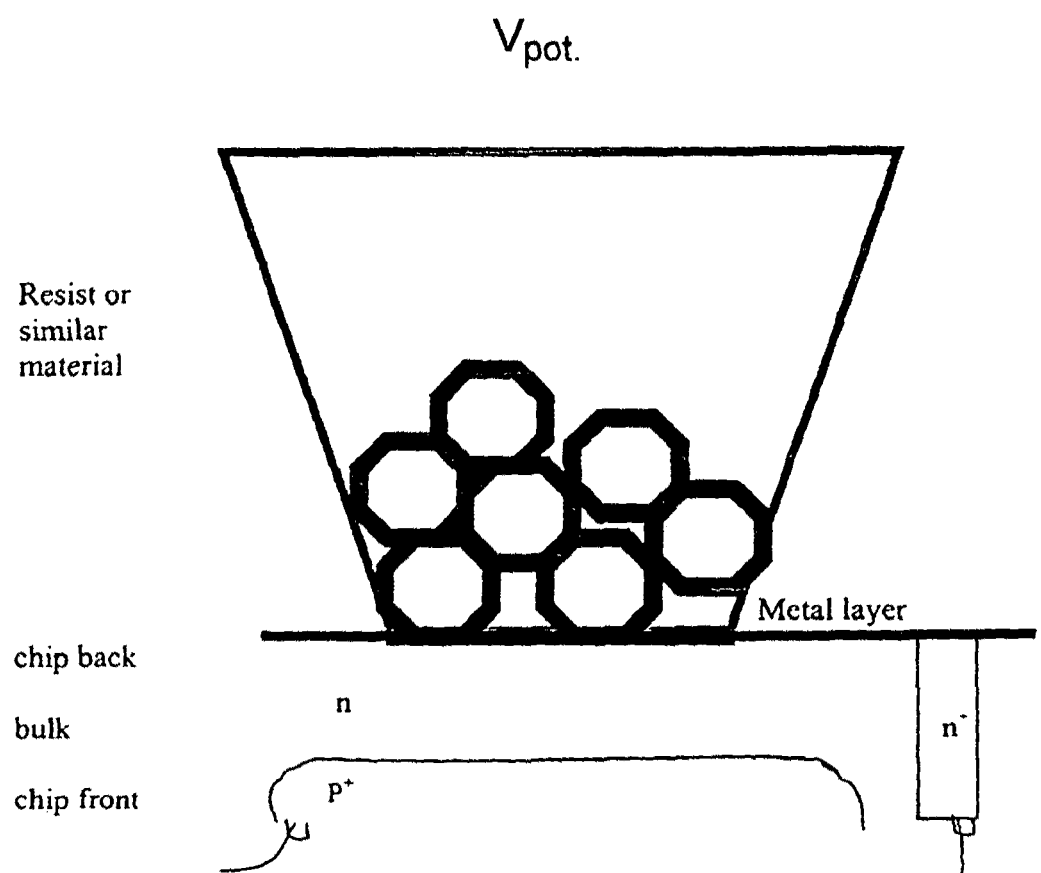
FIG. 16 illustrates a schematic cross section of such a photodiode as shown in FIG. 15 according to one embodiment of the present invention.

By drilling the crater through a region (e.g., region 2 shown in FIG. 14), or into the doped region, light is able to penetrate through the sides and bottom of the crater and reach the interface to region 1. FIG. 16 illustrates a schematic cross section of such a photodiode 210 according to one embodiment of the present invention. As shown, regions 1 and 2 are contacted by wire bonding from the front and the crater is built on the back of the wafer. The Si bulk is about 10 μm thick in the crater region and the diameter of the photodiode is around 50 μm. The highly doped dark blue channel allows for contacting of the n-bulk from the front. The metal layer that distributes the bulk connection can be circular to allow light from the crater to penetrate through to region 2 (P+).

Figure 15:
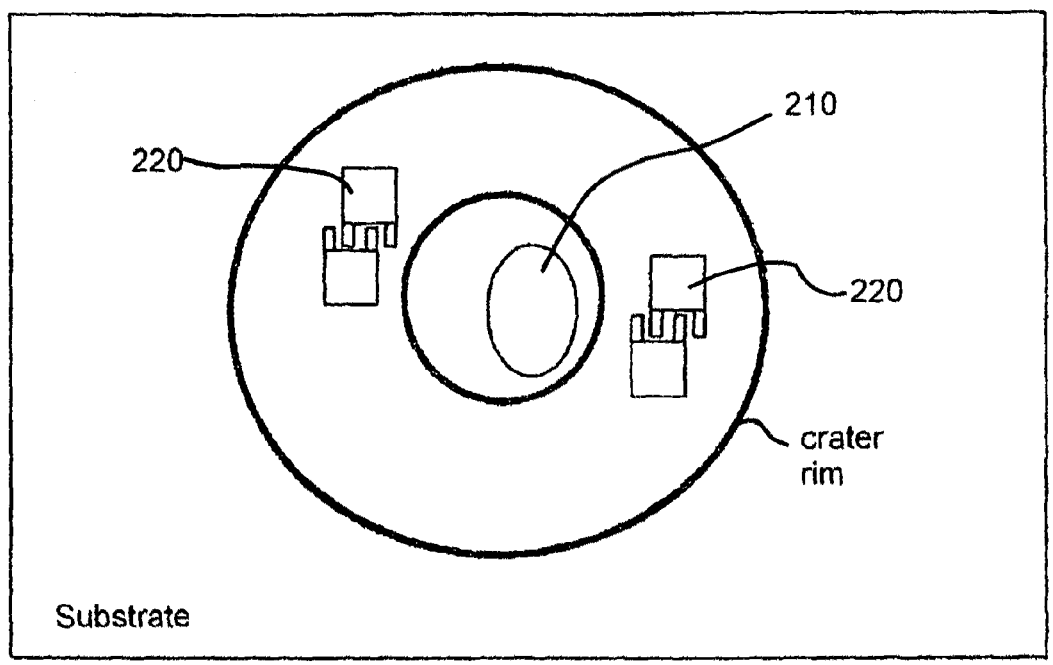
FIG. 15 shows a crater from above according to one embodiment, including three detectors as schematically indicated: a photodiode on the flat and horizontal bottom and two identical capacitors on the sloping insides.

FIG. 15 shows a crater from above according to one embodiment, including three detectors as schematically indicated: a photodiode 210 on the flat and horizontal bottom and two identical capacitors 220 on the sloping insides. The capacitors 220 as shown include four fingers in two electrically isolated halves. Changing properties inside the crater often affect the dielectric constant that in turn changes the capacitance. When connected to a standard detection circuit, each capacitor reveals changes in the dielectric constant inside the crater volume. The same capacitors can be manufactured in almost any shape and their location can be varied, e.g., on the bottom of the crater or near the crater or anywhere on the chip where minute changes in dielectric constant need be monitored. The capacitors can be manufactured using any of numerous well known techniques such as metal deposition, and the two capacitor regions can be electrically contacted from above, through the crater opening.

In one embodiment, an interference filter is deposited across the whole chip, or in selected regions, to provide buried photo detectors with light of only desired or interesting wavelengths. Even if a photo detector is buried inside or on the bottom of a crater it can be covered by a global or local filter patch. Filters can also be designed to have different characteristics on different areas on the chip.

Alternatively or in addition to such photo detectors, one skilled in the art could include, for example, a radiation detector to detect radioactivity incorporated into bio-samples, a wavelength-specific photodetector for distinguishing red and green dyes commonly used in microarrays, a pH sensor to detect chemical environment changes produced by living cells. One skilled in the art could also incorporate a wide range of other sensors and sensing systems for the study of light, radiation, heat, electric signal, magnetic fields, chemical environment, stress or contact, dielectric, surface plasmon resonance effects, thermal environment, pH, capacitance, pressure, acoustic waves, optical polarization, time, etc. Sensors may be supplemented by other micro-components and transducers, such as lasers and photo-emitters, heating elements, cooling and peltier elements, electro-wetting control elements, magnetic or electric field generators, micro-motors or micro force-transducers, resonators, relays and switches, pumps, valves, vibrators, mixers etc. Many other types of sensors, transducers, and micro-components could be incorporated into the invention. Typical factors to consider for incorporating sensors and other elements include exposure to moisture, heat, cold, mechanical stress, electrical charge or shock, magnetic environment, interference, corrosion, metal migration, radiation damage, packaging methodology, fabrication defects and contaminants. Materials such as microfabricated metals, for example, can undergo corrosion and degradation in environments such as aqueous fluids, corrosive gasses, or those with uncontrolled electric discharges. Using indirect force transduction, e.g. through-space fields like magnets, enables useful techniques for isolation of sensitive electronics from the environment. One of ordinary skill will appreciate that coatings, dopings, treatments, chemical modifications, localization of materials or components, etc. used to fabricate micro-components such as sensors are facilitated by the operation of the present invention as an aid to the fabrication process. For example, specific treatments for sensors may be selectively added, modified, excluded, or controlled by opening or closing lids, operating force transduction mechanisms to attract, repel, magnetize, polarize, or otherwise affect the environment of sensors and micro-components during initial fabrication or subsequent "on-site" use or modification in a laboratory or in the field. The localization of lid-particles, for example, inherently uses active elements to fabricate the invention, e.g., by localizing lids to locations lacking appropriate lids, by sensing that the lid has been appropriately localized and by returning data indicating the success, failure, or other aspects or conditions of one or more locations operated to localize lids.

Kovacs, *Micromachined Transducers Sourcebook*, 1998, and Madou, M., *Fundamentals of Microfabrication*, 1997, both of which are hereby incorporated by reference, include numerous sensor types applicable for integration with the platforms of the present invention. Specific sensor types and considerations included therein, and others, include, for example:

1. Photodiodes: generally visible and IR; can be optimized for UV (e.g., Kovacs, p. 400).
2. CMOS pixel sensor, imager, with ~26 µm/side pixel (e.g., Kovacs, p. 399).
3. Metal-semiconductor (schottky) photodiodes that can operate at high frequency in GaAs (e.g., Kovacs, p. 400).
4. Avalanche photodiodes optimizable to provide high gain (equations, e.g., Kovacs, p. 402).
5. MOS-capacitor sensors in CMOS (e.g., Kovacs, p. 409).
6. CMOS sensors configurable to detect the entire visible light spectrum; incident light must be separated into different spectral bands for color imaging. Separation is accomplished by depositing colored filter materials (usually dyed or pigmented polymers) sequentially on the imager's top surface, arranged in a mosaic pattern known as a color filter array (CFA).
7. Direct UV CMOS detectors (e.g., Kovacs, p. 410).
8. Phosphors are sometimes used to make "indirect" photo sensors to convert wavelengths of light invisible to an available sensor into wavelengths it can detect. Scintillation detectors are one such photo sensor (e.g., Kovacs, p. 433). IR up-converting phosphors absorb IR and re-emit in visible.

According to the present invention, sensors may be integrated in many different locations and configurations, for example:

a. A sensor may be provided under an element, e.g., a photodiode under a crater that senses chemiluminescence in the crater—the sensor may be provided at the bottom or floor of a crater, integrated as part of the floor of the crater, or included in a removably attachable module positioned below the chip.

b. A sensor may be provided adjacent to an element, e.g., a photodiode in the wall of a crater, or a radiation detector nearby a crater or coil, affected by radiation in the crater, etc.

c. A sensor may surround an element, e.g., a hole drilled through one or more sensors with a crater inside, a coil wrapped around an element, sensing flux through the coil, a sensor in rim of crater, etc.

d. A location may contain several sensors of the same type or different types, e.g., several sensors in the floor, sensors in floor and wall, sensors in several walls, several sensors adjacent to the element/location, etc.

e. A sensor may be on a different chip (modular), e.g., below the location, above the location, flip-chip bonded to look down, optical fibers routing signals away from each location, micro-optics focusing light from each location onto an array of sensors above the chip, etc.

f. A sensor may have signal routed to it, e.g., a transparent layer provided for routing signals to optical detectors, electrically conductive or magnetically active wires conveying signals to sensors, etc.

g. Sensors may be organized differently in different locations around the chip, e.g., an array of radiation detector elements, separate array of light-detecting elements, etc.

h. Sensors may be used collectively across multiple elements, e.g., sensors between elements—signal at each element due to interpolation, etc i. Sensors may be dual purpose, e.g., sensing and transducing coils.

j. Sensors can be locally passive, e.g., quartz grooves, library-security-like inductive sensors, chemical coating that re-emits light from sample at new wavelength (e.g. absorb or emit wavelength specific to that sensor), etc.

k. Sensors can be multi-component, e.g., inductive coil interacting with lid-bead to detect closure.

When choosing sensors and other components, implementation issues may arise. Compatibility with manufacturing processes and desired assays or applications may become an issue. For example, a gallium-arsenide detector can be very difficult to implement in a CMOS chip system. Additionally, undesired heat generated can affect samples. For example, magnetic coils can generate heat. For protein samples, this can be undesirable. Solutions according to the present invention include increasing windings or amount of conductor to decrease current, adding a peltier or other cooling device, cooling the chip with fluid flow, etc. Such heat can also be harnessed for use, for example to change the rate of local chemical reactions. One skilled in the art can measure factors including heat, or estimate them with software simulations such as those facilitated by the ANSYS software package.

Consideration of power consumption, wire routing, and element control can be important when a chip comprises many micro-components. On-chip electronics to control many elements is facilitated by use of a process allowing basic logic, such as the CMOS process used in standard computer microchip fabrication. BiCMOS, bipolar, galium arsenide, low-temperature co-fired ceramic on metal, metal on glass, plastics, flexible-film circuits, print-on-demand circuits, and many other fabrication processes are possible. For coil fabrication, for example, the width, depth, layer interconnects, and accessible geometry of conductor for fabricating the coils are affected by the manufacturing process chosen. CMOS trace thickness can be on the order of microns. Processes such as electroplating allow thicker traces to be used, resulting in more conducting material, lower current requirements, and less generated heat.

In one embodiment, an insulating/passivating layer is provided to isolate electronics. Moisture, chemical reactions, corrosion, atmospheric contamination, metal migration, and other factors can alter the function of microelectronic components. Conductive electrodes in electrical contact with an aqueous biological sample, for example, can fail or perform anomalously due to reactions between the conductor and ions in the solution. A layer such as parylene, silicon nitride, or a polymer coating that isolates electronics in the microsystem from the sample-containing environment is provided to prevent undesirable failure modes and improve device function. Such layers can also improve the bio-compatibility of the device. For example, many bio-samples may be degraded or altered when exposed to reactive chemical environments near the interface of a liquid and an electrode.

The platforms of the present invention include device components and teach methods that can scale with micro-electronics industry and microfabrication industry processes. Submicron sizes are currently possible, for example techniques from modern commercial processes for manufacturing microprocessors allow wire traces at the 0.18 micron width for conductors, and smaller feature sizes are possible in academic or pre-commercial processes. Fabrication processes in the fields of self-assembling structures and nanotechnology, for example, teach that conducting traces, semiconductor layers, and constituent diodes, microcomponents, or substitutes for microcomponents required for the present invention are possible on size scales of 100 nm, 50 nm, or below.

Larger sizes are also possible, as are uses with other laboratory equipment and methods. An aspect of the present invention is that macro-scopic systems compatible or integratable with standard laboratory equipment are possible. Use of a wide range of existing laboratory equipment, components, protocols, and workflows is possible using the teachings of the present invention. Non-limiting examples of device form-factors compatible with the present invention include 24-, 48-, 96-, 384-, 864-, 1536-, and other-well plates, deep-well, standard-well, flat, concave, convex, patterned, inverted, treated and non-treated plates. Laboratory devices such as mass spectrometers, DNA slide spotting- or sample-deposition robots, fraction collectors, polymerase chain reaction devices, heating blocks, plate-readers, surface-plasmon-resonance equipment, crystallography sample preparation or measurement, and many other devices and protocols can be more easily used with specific geometries, lay-outs, fabrication materials, and other considerations for construction and use that are known for the manufacture and use of prior-art equipment in these situations. The arrangements and devices of the present invention may constructed for use horizontally, vertically, upside-down, in stable or moving environments, shaking or rotating, under low or high frequency controlled or random vibrations, and many other stationary or mobile conditions.

Sizes and geometries of features of devices and arrangements of the present invention can be scaled according to the application, including by analyzing the teachings and properties of existing systems or sizes. For example, filter openings having effective pore sizes including 0.1 um, 0.2 um, 0.4 um, 1, 2, 3 um, 4, 5 um, 8 um, 10 um, 20 um, 30 um, 40 um, 50 um, 75 um, 100 um, 150 um, 200 um, 250 um, 500 um, 1,000 um, etc., may be used Laboratory equipment well diameters including, e.g., 25 mm, 10 mm, 5 mm, 1 mm, 0.5 mm, and others larger and smaller are possible. Volumes including 1E-18 L, 1e-17 L, 1e-16 L, 1e-15 L, 1e-14 L, 1e-13 L, 1e-12 L, 1e-10 L, 1e-9 L, 1e-8 L, 1e-7 L, 1 nl, 5 nl, 10 nl, 25 nl, 50 nl, 100 nl, 250 nl, 500 nl, 1 ul, 2 ul, 5 ul, 10 ul, 20 ul, 50 ul, 75 ul, 100 ul, 200 ul, 500 ul, 1,000 ul, 5,000 ul, and others larger and smaller are desirable in various laboratory and device applications. Individual elements may be round, square, rectangular, grooved, patterned, flat, ridged, etc. and include ring-structures, cross-structures, and many other combinations of these shapes or additional patterns. Elements or parts of elements may be notched or modified at the edges, present as raised or depressed pillars, columns, ridges, rings, squares or rectangles, pyramids, angular or curved structures. Such changes may be used to increase, decrease, selectively or non-selectively alter the transport of samples and materials proximal to an element or location.

The devices and arrangements of the present invention can include one or more coils, electrodes, or other elements jointly controlling access to a region or location. For example, a plurality of crater-openings can connect to the same crater cavity. In one aspect, valves, doors, ports, gates, or other mechanisms are provided for controlling passage through a pre-determined region. A plurality of such regions can collectively control passage into or out of a bottle, tube, chamber, channel system, cavity, or other volume. Controlled and/or monitored passage of materials, particles, fluids, electromagnetic fields including light, radiation, or atoms through an area is possible using the present invention. Sensing such passage, or the conditions of the environment and materials on either side of the controlled-passage area, are possible.

One of ordinary skill should appreciate that by its nature many aspects of the present invention are selectively controllable, for example, the action of coils, plates, electrodes, lids, sensors, and other microcomponents. Analog or digital electronics and other means may be directly fabricated in a substrate, directly attached to a device, or used remotely to control, modify, receive, or transmit data, power, signals, and otherwise communicate with or use the components of the present invention. One of ordinary skill in the computer-memory field, for example, should appreciate that a wide variety of means and well understood practices are available for designing a device including a large number of microelectronic components such as are taught in aspects of the present invention.

Aspects of the present invention also include a data-intensive measurement system, to be optionally used in conjunction with appropriate device drivers; connections to external computing systems; read-out and analysis of the data; data-storage and database systems, data encryption, and data verification techniques; signal processing, correction, compression, enhancement, or modification by statistical and/or machine-learning techniques to insure efficient and accurate use and availability of the communications with and results from components and measurements of the present invention.

In one aspect, low-power versions are intended to enable portability. For example, consumer products such as the Intel Play QX3 microscope may be implemented and powered entirely by a standard USB connection cable to a portable computer. Appropriately fabricated versions of the present invention, for example, a version using CMOS photodiodes and integrated control electronics, may be used as an independently, portably-powered device or directly connected to standard stationary or portable computing systems. Standard USB, SCSI, Firewire, Bluetooth, wireless, fiber-optic, serial cable, parallel cable, ethernet, PCI, zero-insertion-force sockets, PCMCIA or other cartridges, power-line data transmission, infra-red, and radio are a few examples of useful interfaces for associating a device with another system. These and many other interface systems, methods and protocols can be used to connect, communicate with, or provide power to appropriate constituents and forms of the present invention. Such connections may be proximal, such as a packaged device compatible with a standard format socket, or allow a device to be located remotely, such as at the end of a long USB cable. A portable version, for example, could be placed in a specialized environment, such as a heated cell-culture or shaker-room, cold-room, radioactive area, high-pressure or hard-vacuum, harsh chemical environment, or other remote location where the device could continue operation optionally to be later recovered for analysis of samples, or in other environments or uses. For example, appropriately implemented, devices and arrangements according to the present invention could be used to collect and/or analyze samples or environmental conditions over time, as in biohazard monitoring, air-quality monitoring at a hazardous chemical facility, exterior of a submarine near a thermal vent, or aerospace vehicle in high altitude or vacuum. As other examples of use beyond sample trapping, a plurality of samples such as radiation or chemically sensitive materials may be substantially and selectively isolated from their environment. Exposure of a first sample, and later exposure of a second sample, allows time-course measurements including those that expose some samples repeatedly or exposes a fresh sample at each point in time.

Electrically isolated elements or indirect force transduction may not be optimal in all applications. The platforms of the present invention provide for a broad range of force transduction components. For example, direct force transduction means such as one or more electrophoretic terminals can be placed in or near a crater or element, in an embodiment of the present invention. These terminals could be used as a compliment to or replacement for magnetic coils. An embodiment using an electrode in a crater could thus expose a conductor to the environment. This could, for example, be used to controllably create an electrophoretic circuit and drive electrophoresis in a fluid environment. It could also be used to attract or repel charged particles or substances that could directly contact the electrode. The electrode would be directly subject to direct environmental alterations, such as the degradative electrochemistry that can occur on electrodes in many biological environments and fluids. Conductive coatings, gel layers, and other known means may be implemented to control the interaction of the electrode and the environment. In the electrode example, other manufacturing processes, such as standard parylene vapor deposition conformal coating, are useful, but may be more difficult to use when isolating electronics from undesirable interactions with the environment, as conformal coatings like parylene do not ordinarily conduct electricity efficiently. One skilled in the art should readily appreciate the additional steps or treatments typically required to maintain appropriate electrical contact between an electrode and its environment when implementing an application of parylene and other non-conductive coatings.

One skilled in the art should appreciate that the teachings of magnetic coils and fields generally apply to other through-space force transduction methods or electromagnetic elements. For example, one or more electrodes, plates, combs, coils, etc. can be used to create a voltage potential, electric field, or local charge distribution or surface potential. These structures can be used, for example, to create an electric field or potential to transduce force to charged or induced-charge materials, particles or beads, etc. Such plates, coils, wires, and other means can also provide sensing, for example of dielectric or capacitance changes in the environment. In one aspect, the present invention teaches the use of through-space force transducing and/or sensing elements, with, without, or as a replacement for the use of magnetic elements.

Effective force transduction by indirectly or directly creating or sustaining interaction energy at an element is possible with the present invention. For example, contact-adhesion due to complimentary geometry is one technique. In one aspect, a "lock" complimentary to a targeted "key" is provided to affect the localization of the key near the lock. A pocket substantially complimentary in size or geometry to holding a single particle, for example, allows localization of a particle to the pocket with or without other force transducing mechanisms. Coatings, treatments, gels, glues, reactive and non-reactive chemicals can all be used to alter the localization of materials near a pocket, coil, plate, crater, or other structure. Pockets and surface treatments for attraction of single particles, such as those taught in the bead-fiber array technology (see, e.g., Illumina), are useful in biological and other applications. Other geometries, such as flat discs, rectangles, irregular spots, rings, comb structures, grids, or other patterns having, or pre-prepared for having, appropriate chemistries, capture agents, and surface properties are well known in the art. In the biological arts, for example, treatments such as with DNA, antibodies, small molecules, nickel or other metal affinity ligands, sugars and sugar-containing compounds, lipids and modified lipids, and other molecules are commonly used. The arts of chemical engineering, surface chemistry, MEMS, aerospace technology, specialty coatings and many other fields are useful areas teaching well-known modifications of surfaces to increase, decrease, or controllably alter the contact affinity between two or more physical materials.

The present invention is thus useful in a broad variety of applications and environmental conditions that require a commensurate breadth of components, including components that affect the manufacture, packaging, use, and reliability of components in a microsystem.

Additional Aspects

Coils, electrodes, electric plates, and other force transduction mechanisms can be positioned to control particle location and motion in areas besides through an opening. For example, a magnetic coil (or, e.g., electrode) located directly under a crater can be used to retain or repel smaller magnetic (or, e.g., charged) particles trapped inside a crater. A coil (or other element) around or near the middle or lower portion of a crater can be used to retain or repel or otherwise affect localization of magnetic particles trapped inside a crater. Coils, electrodes, and other elements need not surround a crater or other sample-trapping element. For example, an electrode in one side or area of a crater can preferentially attract or repel charged material to that electrode. Magnetic coils including current-carrying wires, electrophoretic terminals or electrodes, electrowetting mechanisms such as surface-tension affecting plates, and other force transducing mechanisms may act similarly. A coil, electrode, or other force transducer on the surface of a chip proximal to an element (e.g., a crater) can be used to alter the localization or motion of materials near that element. For example, a coil, electrode, or other element at one side of a crater can be used to attract or repel a particle or lid. Furthering this example, a coil, or other force transducing element, can be used to localize a lid particle proximal to a crater and controllably determine when that particular lid particle is transferred to the crater for capping with that particular lid particle; extending this with multiple coils, etc., a selective choice of multiple lids or different types of lids may be used for the same crater. Of course, particles other than lids may be controlled and passed to or removed from a crater or other location in a similar fashion.

Alternatives to coils include individual magnetic wires, plates, or other current carrying structures that create magnetic fields. For example, wires running along the surface of a chip will create a magnetic field and thereby transduce force to magnetically active particles or materials. When desired, such forces can be mitigated, for example by including a second wire with current flowing in an opposing direction, preferably with the second wire proximal to and substantially below and parallel to the first.

In some embodiments, forces can be advantageously increased or altered by coordinating external elements or fields in conjunction with elements on the primary substrate. For example two substrates comprising force transduction elements may be placed opposing each other creating dynamically controlled fields between them. For example, two opposing and aligned magnetic coils may be used to create a jointly controlled field. Such a jointly controlled field can be, for example, similar to one as seen between two classical magnets aligned with an interposing gap. By dynamically operating such a field one can, for example, create a controllable dynamic field for selectively attracting or repelling particles including vertically as well as horizontally. For example, one can balance a particle between two elements, or attract or repel a particle from one element for another. For example, one can pass a particle between opposing elements, somewhat similar to passing a particle between two adjacent elements. Decreasing the attractive force of one coil while increasing the attractive force of the second coil can be helpful in this regard, as can repelling with one field while attracting with the other. One of ordinary skill will appreciate these teachings can be applied to other force transduction elements, for example opposing electrodes (e.g. plates) creating an electric field. In addition to dynamic elements, one can advantageously use static or permanent magnetic fields. For example, a uniform magnetic field from a permanent magnet plate below the substrate, e.g. a plate that is large when compared with the total area of invention, can be used to create a substantially uniform magnetic field that increases the force on or between magnetic particles, or magnetic particles and elements of a device of the invention. Permanent magnets, such as rare earth magnets, may be formed in sheets or laminates for placement or inclusion as desired. Depending on factors including element configurations, sizes, distances, field strengths, particles sizes and compositions, etc., field strengths of between 0.01 gauss and 500 mT, or higher or lower can be achieved.

In some embodiments, particles with an induced magnetic field (e.g., ferromagnetic or super-paramagnetic particles) can stick together or "clump" in solution. In some situations, this can be undesirable. Reducing stiction between particles, inducing opposite or having fixed charges in particles, and other methods can be used to control particle clumping. Other methods are also possible. For example, vibrations (e.g., low frequency, high frequency, acute "jolts", or ultrasonic vibrations) can be applied to the invention to "de-clump" particles. For example, time-varying fields, (e.g., time varying magnetic or electric fields) can similarly be used to induce motion in the particles that mitigates or breaks up clumps. For example, randomly or rapidly changing, alternating, or varying fields (e.g., electric or magnetic) or force transduction element action can be used to induce motion in particles and induce disassociation of clumps. Random motion of particles, e.g., as induced by force transduction elements (e.g., similar to de-clumping motion as taught by ultra sonic vibration of particles for de-clumping), can be used in de-clumping particles. De-clumping can also be achieved, for example, by macroscopic devices or equipment. External magnets vibrators, charges, electrodes (e.g. plates), etc. can be used to create substantially ambient conditions affecting substantially all particles (or samples, locations, materials, etc.).

In some aspects, particles of different physical characteristic can be controlled differently. For example, particles of different effective radius, density, inertia, or other properties will respond differently to forces such as flow of surrounding media, bulk pressure or fluid density, or time-varying forces. For example, high-frequency forces (e.g. magnetic fields) will cause motion in smaller particles but not larger particles, as smaller particles can be moved on a time frame where the inertia or Reynolds-number effects of larger particles prevents said larger particles from achieving substantial motion.

Through the various methods of inducing motion, localization, attraction, repulsion, non-interaction or canceling of attraction, etc., one of ordinary skill will appreciate that mobile particles, samples, or other materials may be de-localized from a location and thereby be enabled to be removed from the invention. For example, in a pocket or crater embodiment, one can reduce the adhesion or attractive force to release one or more particles. If a coil or force transduction element is present it can be used to achieve a sustained or transient repulsive force, e.g., a pulse from a magnetic or electric coil or electrode to loosen or repel a particle. External sources of force, such as a magnet on a rod or externally applied magnetic field, can be used to recover a particle for removal from the system (e.g., for later analysis, transport, or storage, such as with a mass spectrometry or PCR analysis device). Advantageously, removal and analysis of sample or particles from a device according to the present invention are not typically available with other systems.

While the invention has been described by way of example and in terms of the specific embodiments, it is to be understood that the invention is not limited to the disclosed embodiments. To the contrary, it is intended to cover various modifications and similar arrangements, in addition to those discussed above, as would be apparent to those skilled in the art. Therefore, the scope of the appended claims should be accorded the broadest interpretation so as to encompass all such modifications and similar arrangements.

The invention claimed is:

1. An analytical device comprising:
   a substrate having a first surface;
   at least one location on the first surface of the substrate;
   a first field element configured to generate a first magnetic field that encompasses the at least one location; and
   at least one magnetic force transduction element located proximal the at least one location and configured to generate a second magnetic field that applies a force to at least one particle,
   wherein the first field element and the magnetic force transduction element are configured such that the first magnetic field increases the force on the particle applied by the magnetic force transduction element and such that the increased force allows the second magnetic field to localize the particle to the at least one location.

2. The device of claim 1, wherein the at least one magnetic force transduction element includes at least one conducting coil, the conducting coil configured for producing a magnetic field when a current is applied thereto.

3. The device of claim 2, wherein the at least one conducting coil is located around a perimeter of the at least one location on the first surface of the substrate.

4. The device of claim 2, wherein the device is configured for independently and controllably localizing one or more particles that each comprise a magnetic or magnetizable bead.

5. The device of claim 1, wherein the first field element comprises a permanent magnet.

6. The device of claim 1, wherein the first magnetic field is substantially uniform.

7. The device of claim 1, further comprising a microvalve comprising an opening proximal to the first surface, wherein the first field element and the at least one magnetic force transduction element are configured to control movement of the particle relative to the opening to control passage through the opening.

8. The device of claim 1, wherein the increased force is comprises a sustained repulsive force.

9. The device of claim 1, wherein the first field element and the at least one magnetic force transduction element are configured to localize the particle to the location in such a manner as to induce flow in a surrounding fluid, to block flow in a surrounding fluid, or to achieve micromixing.

10. The device of claim 1, wherein the at least one location comprises a first and second location, and the first field element and the magnetic force transduction element are configured to pass the particle between those locations.

11. The device of claim 1, wherein the at least one magnetic force transduction element comprises a first and second magnetic coil, and wherein the first and second magnetic coils are configured to localize the particle in a manner that decreases an attractive force of the first coil while increasing an attractive force of the second coil.

12. The device of claim 1, wherein the at least one location comprises a multiplicity of locations each being proximal to at least one of the force transducing elements for localizing at least one particle to each of the locations.

13. The device of claim 1, wherein the first field element and the at least one magnetic force transduction element are configured to move the particle from one of the locations that is determined prior to the moving and another of the locations that is determined prior to the moving.

14. The device of claim 1, wherein the first field element and the at least one magnetic force transduction element are configured to move a redetermined one of a plurality of particles from one of the locations to another of the locations.

15. The device of claim 1, wherein the at least one magnetic force transduction element further comprises a plurality of force transduction elements configured to jointly control access to a region proximal to the substrate or to the at least one location.

16. The device of claim 1, further comprising a communication path coupled to the at least one magnetic force transduction element, the communication path configured to provide a control signal to control the generation of the second magnetic field by the at least one magnetic force transduction element.

17. The device of claim 1, wherein the at least one location comprises an array of locations, wherein each of the locations has a magnetic force transduction element configured to generate a magnetic field, and wherein the first field element is configured to generate the first magnetic field such that it encompasses the array of locations.

18. The device of claim 1, wherein the at least one location comprises an array of locations, and further comprising a sensor proximal to each of a multiplicity of the locations.

19. The device of claim 1, wherein the at least one location comprises an array of locations, and further comprising a pocket or a crater in the first substrate proximal to each of a multiplicity of the locations.

20. The device of claim 1, wherein the at least one location comprises an array of locations, each location comprising a coil, the coils formed in a layered structure with a first layer having a first coil layered on top of a second coil on a second layer, and further comprising an insulating layer in between the first and second layers, the coils controllable independently of one another.

* * * * *